(12) United States Patent
Amengual et al.

(10) Patent No.: US 11,597,933 B2
(45) Date of Patent: Mar. 7, 2023

(54) COMBINATION THERAPY OF LYMPHOMA

(71) Applicant: The Trustees of Columbia University in the City of New York, New York, NY (US)

(72) Inventors: Jennifer Effie Amengual, Scarsdale, NY (US); Jennifer Lue, New York, NY (US); Owen A. O'Connor, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 167 days.

(21) Appl. No.: 16/758,996

(22) PCT Filed: Nov. 29, 2018

(86) PCT No.: PCT/US2018/063060
§ 371 (c)(1),
(2) Date: Apr. 24, 2020

(87) PCT Pub. No.: WO2019/108789
PCT Pub. Date: Jun. 6, 2019

(65) Prior Publication Data
US 2020/0263185 A1 Aug. 20, 2020

Related U.S. Application Data

(60) Provisional application No. 62/591,868, filed on Nov. 29, 2017.

(51) Int. Cl.
| | | |
|---|---|---|
| *A61K 35/17* | (2015.01) | |
| *G01N 33/50* | (2006.01) | |
| *C12N 15/113* | (2010.01) | |
| *A61P 35/00* | (2006.01) | |
| *A61K 31/167* | (2006.01) | |
| *A61K 31/18* | (2006.01) | |
| *A61K 31/4045* | (2006.01) | |
| *A61K 31/4545* | (2006.01) | |
| *A61K 31/496* | (2006.01) | |
| *A61K 31/5377* | (2006.01) | |
| *A61K 38/15* | (2006.01) | |

(52) U.S. Cl.
CPC ........ *C12N 15/1137* (2013.01); *A61K 31/167* (2013.01); *A61K 31/18* (2013.01); *A61K 31/4045* (2013.01); *A61K 31/4545* (2013.01); *A61K 31/496* (2013.01); *A61K 31/5377* (2013.01); *A61K 38/15* (2013.01); *A61P 35/00* (2018.01); *C12N 2320/31* (2013.01)

(58) Field of Classification Search
CPC combination set(s) only.
See application file for complete search history.

(56) References Cited

U.S. PATENT DOCUMENTS

| | | |
|---|---|---|
| 8,257,928 B2 | 9/2012 | Weaver et al. |
| 9,364,500 B2 | 6/2016 | Nezami |
| 9,428,813 B2 | 8/2016 | Kebebew et al. |
| 9,476,100 B1 | 10/2016 | Frumkin et al. |
| 9,534,259 B2 | 1/2017 | Zhang et al. |
| 9,556,430 B2 | 1/2017 | Polyak et al. |
| 9,598,735 B2 | 3/2017 | Song et al. |
| 2015/0320754 A1 | 11/2015 | Kutok et al. |
| 2016/0193239 A1 | 7/2016 | Baylin et al. |
| 2016/0317657 A1 | 11/2016 | Walter et al. |
| 2016/0339035 A1 | 11/2016 | Berger et al. |

FOREIGN PATENT DOCUMENTS

| | | |
|---|---|---|
| WO | 2014/071109 A1 | 5/2014 |
| WO | 2017/019721 A2 | 2/2017 |
| WO | 2017/132518 A1 | 8/2017 |
| WO | 2017/157825 A1 | 9/2017 |

OTHER PUBLICATIONS

Lue et al., "Epigenetic Targeting with EZH2 and HDAC Inhibitors Is Synergistic in EZH2 Deregulated Lymphomas," Blood 128(22): 839 (Jan. 2016) (Year: 2016).*
Morera et al., "Targeting histone methyltransferases and demethylases in clinical trials for cancer therapy," Clin. Epigenetics 8:57 pp. 1-16 (Epubl. May 2016) (Year: 2016).*
Glaser, "HDAC inhibitors: clinical update mechanism based potential," biochemical pharmacology 74:659-671 (2007) (Year: 2007).*
Velichutina et al. "EH2-mediated epigenetic silencing in germinal center B cells contributes to proliferation and lymphomagenesis," Blood, 2010, vol. 116, No. 24, pp. 5247-5255.
Lue et al. "839: Epigenetic targeting with EZH2 and HDAC inhibitors is synergistic in EZH2 deregulated lymphomas," Blood, 2016, vol. 128, No. 22, p. 839.
Lue et al. "259: Dual inhibition of EZH2 and HDAC is synergistic in EZH2 dysregulated lymphomas," Hematol Oncol, 2017, vol. 35, No. S2, p. 254.
Jiang Y, Melnick A. The Epigenetic basis of diffuse large B-cell lymphoma. Semin Hematol. 2015; 52(2): pp. 86-96.
Raut S, Chakrabarti PP. Management of relapsed-refractory diffuse large B cell lymphoma. South Asian J Cancer. 2014; 3(1): pp. 66-70.
Berg et al., A transgenic mouse model demonstrating the oncogenic role of mutations in the polycomb-group gene EZH2 in lymphomagenesis. Blood. 2014; 123(25): pp. 3914-3924.
Shaknovich R, Melnick A. Epigenetics and B-cell Lymphoma. Curr Opin Hematol. 2011; 18(4): pp. 293-299.
Pera et al., Combinatorial epigenetic therapy in diffuse large B cell lymphoma pre-clinical models and patients. Clin Epigenetics. 2016; 8(79).
International Search Report and Written Opinion in corresponding PCT Application No. PCT/US2018/063060, dated Feb. 21, 2019.

(Continued)

*Primary Examiner* — Julie Ha
*Assistant Examiner* — Kristina M Hellman
(74) *Attorney, Agent, or Firm* — Leason Ellis LLP

(57) ABSTRACT

The present disclosure provides for methods and compositions for treating cancer. A subject having lymphoma is administered an EZH2 inhibitor and an HDAC inhibitor. The combination of the EZH2 inhibitor and the HDAC inhibitor produces a synergistic effect on the cancer compared to the effect of the EZH2 inhibitor or the HDAC inhibitor alone.

15 Claims, 21 Drawing Sheets

(56) References Cited

OTHER PUBLICATIONS

Fiskus et al.: "Combined epigenetic therapy with the histone methyltransferase EZH2 inhibitor 3-deazaneplanocin A and the histone deacetylase inhibitor panobinostat against human AML cells": Blood, 2009, vol. 114 / Issue 13, pp. 2733-2743.

Juergens et al.: "Combination epigenetic therapy has efficacy in patients with refractory advanced non-small cell lung cancer": Cancer Discov., 2011, vol. 1 / Issue 7, pp. 598-607.

Connolly et al.: "Combination Epigenetic Therapy in Advanced Breast Cancer with 5-Azacitidine and Entinostat: A Phase II National Cancer Institute/Stand Up to Cancer Study": Clin. Cancer Res. 2016, 23(11):2691-2701.

Takashina et al.: "Combined inhibition of EZH2 and histone deacetylases as a potential epigenetic therapy for non-small-cell lung cancer cells": Cancer Sci., 2016, vol. 107 / Issue 7, pp. 955-962.

Lue et al.: "Epigenetics and Lymphoma—Can We Use Epigenetics to Prime or Reset Chemoresistant Lymphoma Programs?", Lymphomas in Current Oncology Reports, 2015, 17(9):40.

Amengual et al.: "Manipulating the Epigenome in Germinal Center-Derived Lymphomas: Is it Getting Easier and EZier?", Clin Cancer Res. 2014,20(12): 3047-3049.

\* cited by examiner

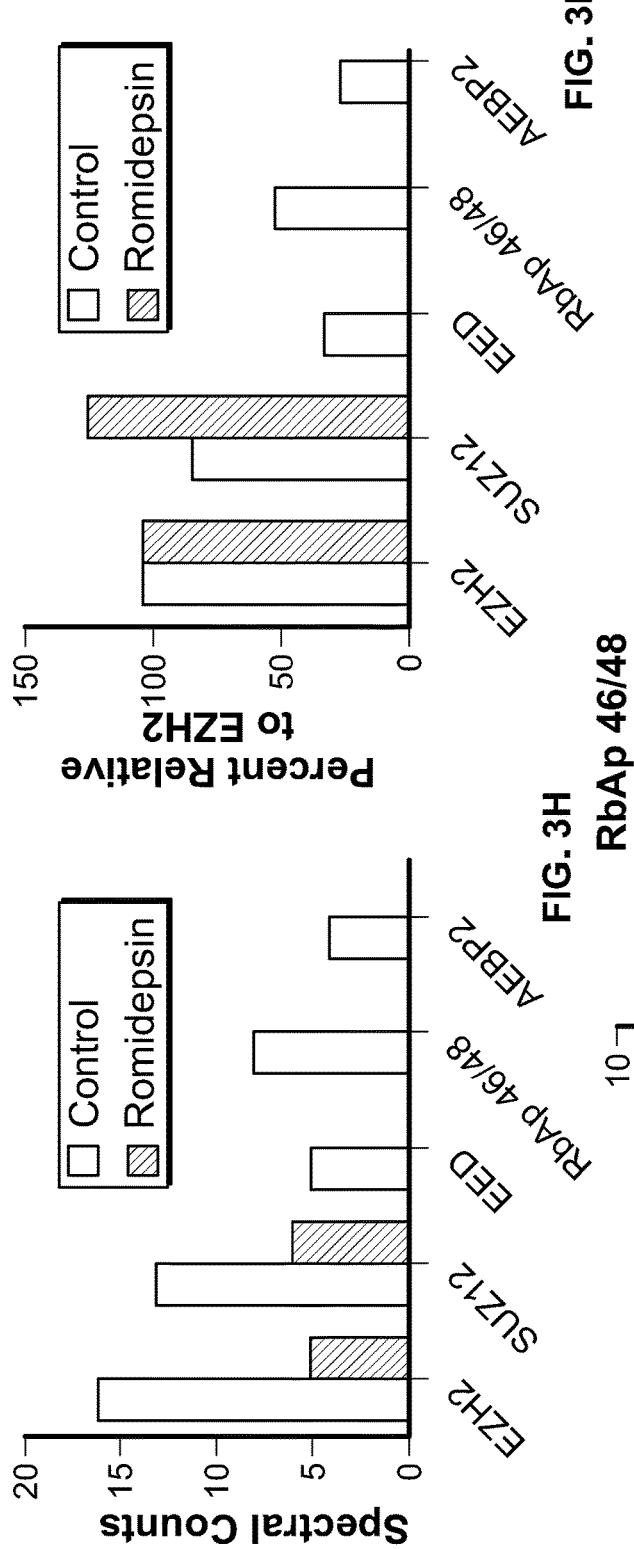
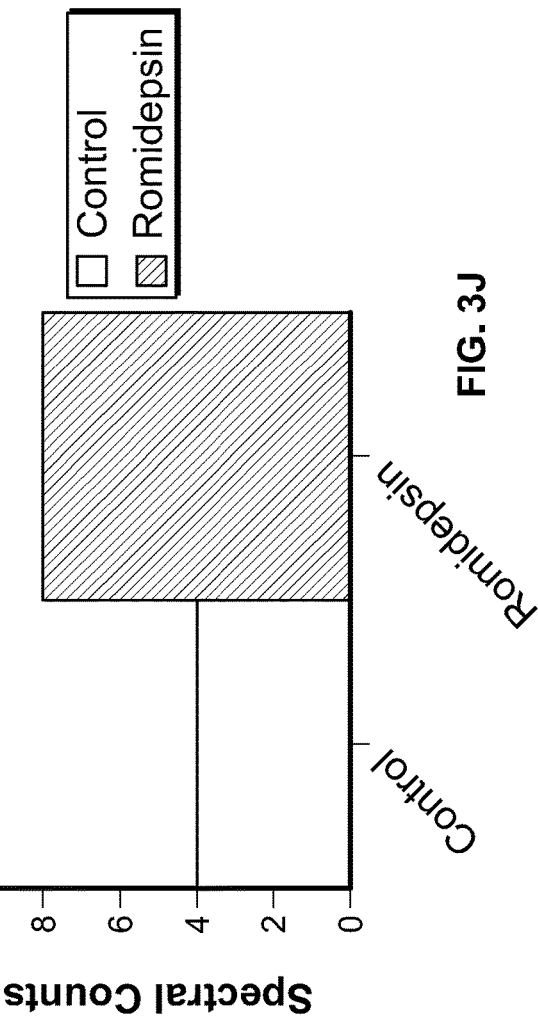
FIG. 3H
FIG. 3I
FIG. 3J

| AUC 0-Last (h*ng/mL) | Tmax (Hours) | Cmax (ng/mL of Serum) |
|---|---|---|
| 5.51 | 0.25 | 98.24 |
| Serum | | |

| AUC 0-Last (h*ng/mL) | Tmax (Hours) | Cmax (ng/mL of Serum, ng/g of Tumor) |
|---|---|---|
| 2828.57 | 0.25 | 1657.54 |
| - | 24 | 140.19 |
| Serum | | |
| Tumor | | |

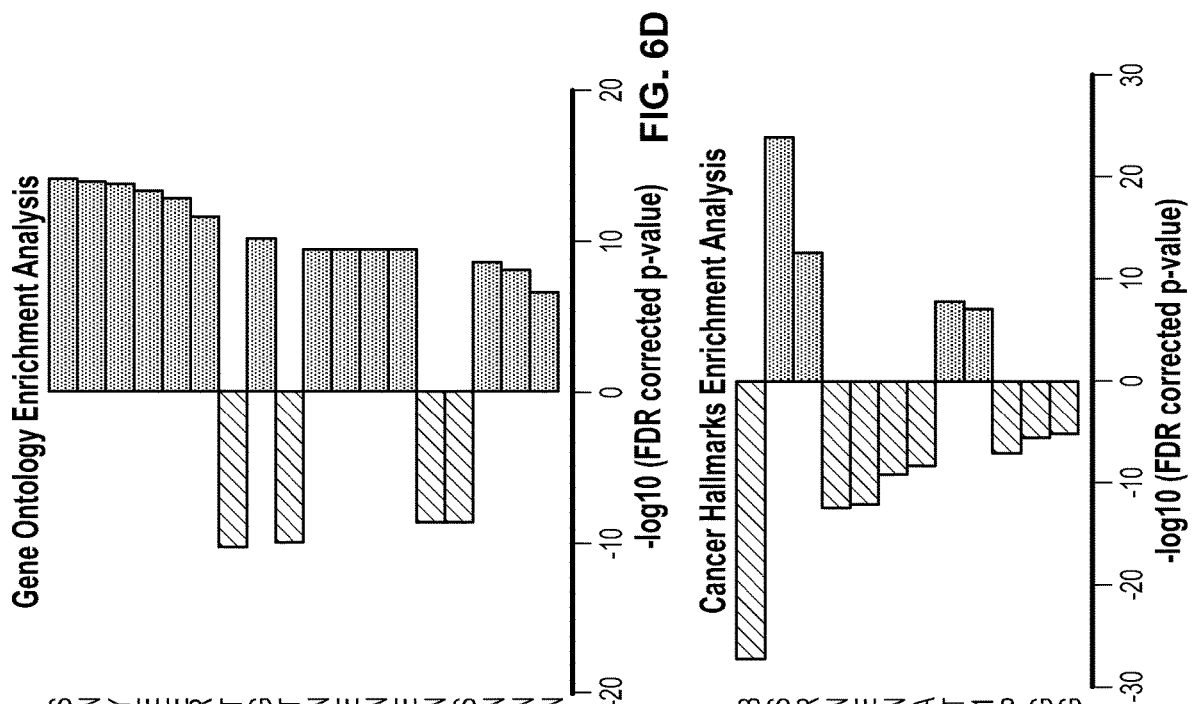
FIG. 6D
FIG. 6E
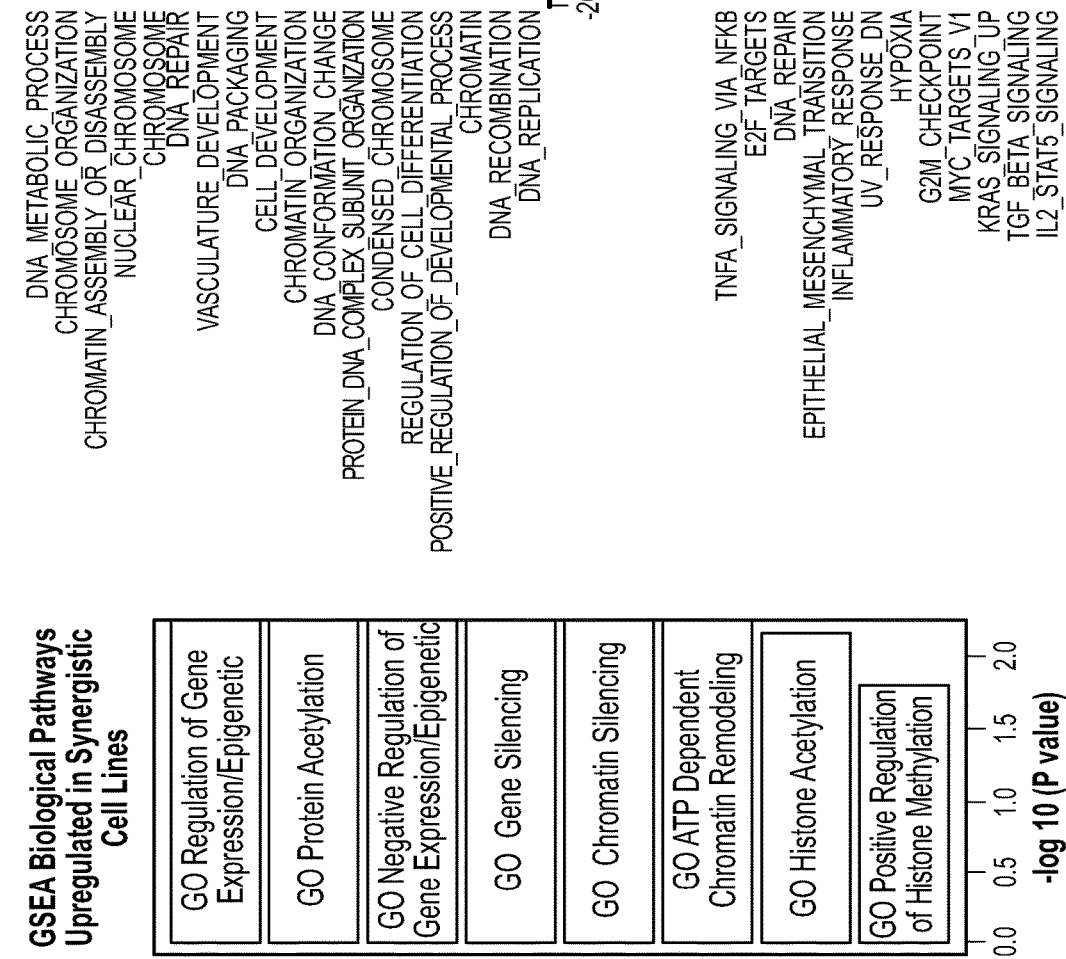
FIG. 6C

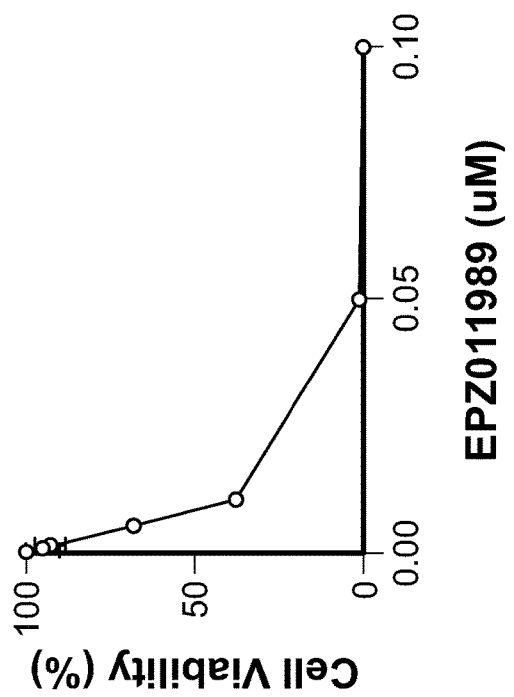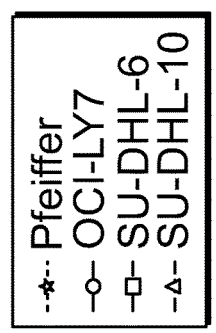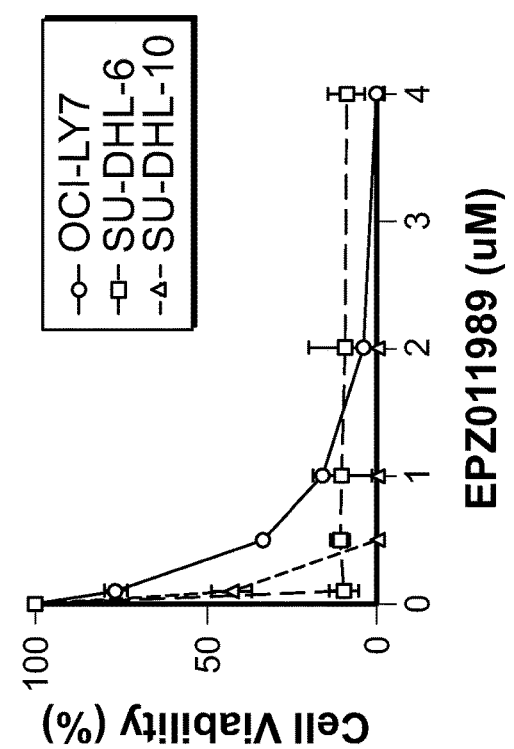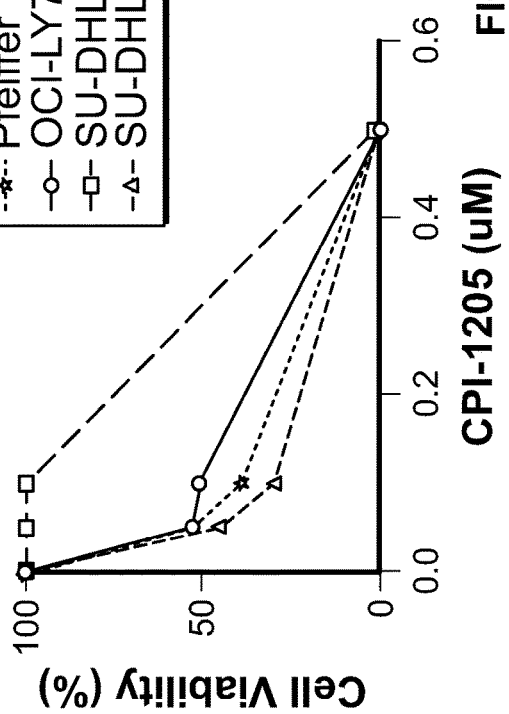
FIG. 8A
FIG. 8B
FIG. 8C

COMBINATION THERAPY OF LYMPHOMA

CROSS REFERENCE TO RELATED APPLICATION

This application claims priority to U.S. provisional application No. 62/591,868, filed on Nov. 29, 2017, the contents of which are hereby incorporated by reference in their entirety.

FIELD OF THE INVENTION

The present invention relates to the treatment of lymphoma. More particularly, the present invention relates to the treatment of EZH2-dysregulated lymphoma by administering an EZH2 inhibitor and an HDAC inhibitor.

BACKGROUND

Diffuse large B-cell lymphoma (DLCBL) is the most common type of lymphoma. Knowledge of the molecular pathogenesis of DLBCL led to classifying this disease into germinal center (GC) and activated B-Cell (ABC) subtypes. The GC-subtype is driven by mutations leading to transcriptional silencing whereas the ABC-subtype is driven by unchecked activation of NFkB. Therapies such as ibrutinib and lenalidomide are in the final stages of development for ABC-DLCBL, however the same success has not been realized for GC-DLCBL, which accounts for more than 60% of DLBCL. 30% of patients with GC-DLBCL treated with standard therapy will relapse and less than half of these patients will be eligible for intensive salvage therapy. Thus, these patients represent an unmet need as there are limited-to-no targeted approaches for salvaging patients with relapsed and refractory GC-DLBCL.

Within the GC, B-lymphocytes undergo somatic hypermutation and isotypic switching in order to build a diverse repertoire of antibodies serving as the foundation of humoral immunity. BCL6 is central to this process and acts as a transcriptional repressor. Epigenetic influences have also been implicated in the GC reaction, contributing to transcriptional repression of cell cycle regulators, DNA damage repair, and differentiation factors. These include histone methyltransferases and histone acetyltransferases (HATs).

Enhancer of Zeste Homolog 2 (EZH2) is highly upregulated during the GC reaction, where B-cells undergo somatic hypermutation. EZH2 is critical in the GC reaction and serves as the catalytic subunit of the Polycomb Repression Complex 2 (PRC2), inducing tri-methylation of histone 3 lysine 27 (H3K27me3), a marker of transcriptional repression[1]. During the GC reaction, the PRC2 complex recruits histone deacetyltransferase (HDAC) 1/2 and DNA methyltransferases (DNMT) to further inhibit transcription[2,3].

Disturbances in epigenetic pathways have been implicated in the pathogenesis of B-cell and T-cell lymphomas (TCL). Aberrancy of histone methyltransferases, such as EZH2, have been associated with the development of lymphomas, particularly GC-derived lymphomas, including diffuse large B cell lymphoma (DLBCL) and follicular lymphoma (FL)[4,5]. Activating mutations in EZH2 have been implicated in 22% of GC-DLBCL and 7-12% of FL[4,5]. EZH2 dysregulation has been implicated in other lymphoma subtypes, including overexpression in some subtypes of TCL[6-9]. Given the prevalence of EZH2 dysregulation in several malignancies, EZH2 inhibitors have been developed, and demonstrate superior efficacy in mutated EZH2 GC-derived lymphoma cell lines compared to wildtype EZH2 cell lines[10-12]. The preclinical activity of the EZH2 inhibitors in B-cell lymphomas has been replicated in the clinic by tazemetostat, a first-in-class EZH2 inhibitor, which demonstrated an overall response rate of 38% in a phase I clinical trial[13,14]. Notably, clinical responses were achieved irrespective of EZH2 mutational status, but was more common in patients with mutations.

Also contributing to GC-lymphomagenesis is the haplo-insufficiency of histone acetyltransferases (HATs). HATs control the addition of acetyl groups on histones in order to promote an open chromatin state, allowing for transcription. Mutations leading to loss of function of HATs, specifically EP300 and CREBBP, are found in 39% of GC-DLBCLs and 41% of FLs, and the presence of these mutations are thought to predict sensitivity to HDAC inhibitors[16,17]. Vorinostat, an HDAC inhibitor, was the first epigenetic drug to gain FDA approval, specifically indicated in patients with relapsed/refractory TCL. Two other HDAC inhibitors, romidepsin and belinostat, have gained approval for the treatment of TCL, while panobinostat has been approved for the treatment of relapsed/refractory multiple myeloma. However, despite the robust link between epigenetic dysregulation and tumorigenesis in several malignancies, few diseases have demonstrated clinical benefit with single agent epigenetic targeting therapy, including GC-derived B-cell lymphomas.

EZH2 is a histone methyltransferase responsible for enforcing transcriptional repression. BCL6 recruits histone deacetylase (HDACs) leading to the deacetylation of histone. This action is counterbalanced by HATs which promotes histone acetylation and transcriptional activation. Recent evidence has shown that derangements in expression of epigenetic modifiers contribute to GC-lymphomagenesis. BCL6 is mutated in 73% of GC-DLBCL. Gain of function mutations in EZH2 are found in 22% of GC-DLBCLs. Heterozygous inactivating mutations of HATs are found in 39% of GC-DLBCLs, and are linked to a more aggressive course.

The acetylation state of a protein is controlled by the activity of two groups of enzymes, histone acetyl transferases (HATs) and histone deacetylases (HDACs). Modulation of the acetylation state of histones, transcription factors, and other regulatory proteins is known to influence their activity. The HATs transfer acetyl-groups to protein, while HDACs remove acetyl-groups. An example of this is the acetylation of histone. Acetylation of histone is mediated by HATs and leads to transcriptional activation, whereas deacetylation by HDACs results in transcriptional repression. An example of these effects on non-histone proteins is seen with the Bcl6: p53 Axis in GC-DLBCL. There is an inverse relationship between Bcl6 and p53, the functional status of which is linked to each transcription factor's degree of acetylation. Acetylation abrogates the effects of Bcl6, an oncogene, but activates p53, a tumor suppressor. Work performed by Pasqualucci and colleagues demonstrated that mutations in HAT enzymes (p300 and CBP) occur in 39% of GC-DLBCL. These mutations abrogate the ability of HAT enzymes to catalyze acetylation. As such, mutated CBP leads to the impaired ability to acetylate BCL6, a transcriptional repressor and master regulator of the germinal center. Acetylation of BCL6 abrogates its effects, whereas the lack of acetylation allows for transcriptional repression imposed by BCL6. Conversely, HAT mutations led to impaired acetylation of p53 which compromised its effects as a tumor suppressor.

Small molecule inhibitors of HDACs help maintain transcriptionally active chromatin, theoretically allowing for expression of tumor suppressor genes. Three HDAC inhibitors, vorinostat, belinostat, and romidepsin have been approved by the FDA for the treatment of T-cell lymphoma. Despite approval in T-cell lymphoma, single agent HDAC inhibitors have demonstrated limited activity in relapsed DLBCL.

SUMMARY

The present disclosure provides for a method of treating lymphoma in a subject. The method may comprise administering an EZH2 inhibitor and an HDAC inhibitor to the subject.

The administration of the EZH2 inhibitor and the HDAC inhibitor may produce a synergistic effect on the lymphoma compared to an effect of the EZH2 inhibitor alone or an effect of the HDAC inhibitor alone. For example, the administration of the EZH2 inhibitor and the HDAC inhibitor may result in a synergistic increase in apoptosis of cancer cells. The administration of the EZH2 inhibitor and the HDAC inhibitor may result in a synergistic reduction in tumor volume. The administration of the EZH2 inhibitor and the HDAC inhibitor may result in a synergistic reduction in cancer cell viability.

The present disclosure provides for a method of treating lymphoma cells. The method may comprise contacting the lymphoma cells with an EZH2 inhibitor and an HDAC inhibitor.

The contacting of the EZH2 inhibitor and the HDAC inhibitor with the lymphoma cells may produce a synergistic effect on the lymphoma cells compared to an effect of the EZH2 inhibitor alone or an effect of the HDAC inhibitor alone. The contacting may result in a synergistic increase in apoptosis of cancer cells. The contacting may result in a synergistic reduction in cancer cell viability.

Also encompassed by the present disclosure is a method of treating lymphoma in a subject. The method may comprise administering to the subject a BCL2 inhibitor, an EZH2 inhibitor, and an HDAC inhibitor.

The administration of the BCL2 inhibitor, the EZH2 inhibitor and the HDAC inhibitor may produce a synergistic effect on the lymphoma compared to an effect of the BCL2 inhibitor alone, an effect of the EZH2 inhibitor alone or an effect of the HDAC inhibitor alone. For example, the administration of the BCL2 inhibitor, the EZH2 inhibitor and the HDAC inhibitor may result in a synergistic increase in apoptosis of cancer cells. The administration of the BCL2 inhibitor, the EZH2 inhibitor and the HDAC inhibitor may result in a synergistic reduction in tumor volume. The administration of the BCL2 inhibitor, the EZH2 inhibitor and the HDAC inhibitor may result in a synergistic reduction in cancer cell viability.

The present disclosure provides for a pharmaceutical composition comprising a first amount of an EZH2 inhibitor and a second amount of an HDAC inhibitor.

The pharmaceutical composition may produce a synergistic effect on lymphoma compared to an effect of the first amount of the EZH2 inhibitor alone or an effect of the second amount of the HDAC inhibitor alone.

The present disclosure provides for a pharmaceutical composition comprising a first amount of an EZH2 inhibitor, a second amount of an HDAC inhibitor, and a third amount of a BCL2 inhibitor.

The pharmaceutical composition may produce a synergistic effect on lymphoma compared to an effect of the first amount of the EZH2 inhibitor alone, an effect of the second amount of the HDAC inhibitor alone, or an effect of the third amount of the BCL2 inhibitor alone.

The lymphoma may be an EZH2-dysregulated lymphoma. The EZH2-dysregulated lymphoma may comprise a gain-of-function mutation in an EZH2 gene. The EZH2-dysregulated lymphoma may be germinal center (GC) derived lymphoma. The EZH2-dysregulated lymphoma may be germinal center (GC) diffuse large B-cell lymphoma (GC-DLCBL), or adult T-cell leukemia lymphoma (ATLL).

The lymphoma may be diffuse large B-cell lymphoma (DLCBL). The lymphoma may be germinal center (GC) diffuse large B-cell lymphoma (GC-DLCBL), or non-GC-DLCBL. The lymphoma may be activated B-Cell (ABC) diffuse large B-cell lymphoma (ABC-DLCBL). The lymphoma may be relapsed or refractory lymphoma, B-cell lymphoma, T-cell lymphoma, GC-derived B-cell lymphoma, follicular lymphoma (FL), mantle cell lymphoma (MCL), mutant follicular lymphoma, and/or double-hit lymphoma.

The present inhibitors (e.g., the EZH2 inhibitor, the HDAC inhibitor, and/or the BCL2 inhibitor) may be a small molecule, a polynucleotide, a polypeptide, or an antibody or antigen-binding portion thereof. In one embodiment, the polynucleotide is a small interfering RNA (siRNA) or an antisense molecule.

The EZH2 inhibitor may be GSK126, tazemetostat, EPZ-011989, CPI-1205, or combinations thereof.

The HDAC inhibitor may be romidepsin, vorinostat, belinostat, panobinostat, or combinations thereof.

The EZH2 inhibitor and the HDAC inhibitor (and the BCL2 inhibitor) may be administered simultaneously, sequentially or separately.

The EZH2 inhibitor and the HDAC inhibitor (and the BCL2 inhibitor) may be administered together in a pharmaceutical composition.

The EZH2 inhibitor and the HDAC inhibitor (and the BCL2 inhibitor) may be administered in separate pharmaceutical compositions.

The EZH2 inhibitor, and/or the HDAC inhibitor, and/or the BCL2 inhibitor, may be administered orally, intravenously, intramuscularly, topically, arterially, or subcutaneously.

The subject may be a mammal, such as a human.

The subject may test positive for an EZH2 gene mutation (which, e.g., may result in EZH2 overexpression).

The subject may do not manifest a hematologic dose-limiting toxicity during treatment. The hematologic dose-limiting toxicity may comprise neutropenia, febrile neutropenia, thrombocytopenia, or combinations thereof.

In one embodiment, dual inhibition of EZH2 and HDAC synergistically treats lymphomas with epigenetic deregulation (dysregulation). For example, GSK126 and romidepsin synergize in lymphomas with EZH2 derangement, inhibit H3K27Me3 and histone deacetylation, disassemble PRC2 complex, and increase expression of p21. In another example, HDAC 1/2 inhibitor synergizes with GSK126 in GC-DLBCL cell lines.

A method of treating a patient with an EZH2-dysregulated lymphoma is provided, the method comprising administering to the patient a therapeutically effective amount of an EZH2 inhibitor and an HDAC inhibitor. In an aspect of the invention, the EZH2 inhibitor is GSK126, tazemetostat, EPZ-011989 or CPI-1205. Further, in aspects of the invention, the HDAC inhibitor is romidepsin, forinostat, belinostat, or panobinostat.

The EZH2 inhibitor and HDAC inhibitor may be administered together in a pharmaceutical composition. In other aspects, the EZH2 inhibitor and HDAC inhibitor may be administered in separate pharmaceutical compositions, wherein the EZH2 inhibitor pharmaceutical composition is administered prior to the HDAC inhibitor pharmaceutical composition, the HDAC inhibitor pharmaceutical composition is administered prior to the EZH2 pharmaceutical composition, or the HDAC inhibitor pharmaceutical composition and the EZH2 pharmaceutical composition are administered at about the same time.

The amount of EZH2 inhibitor administered to the patient may range from about 0.01 mg/kg to about 50 mg/kg. In one embodiment, the EZH2 inhibitor is administered to the patient twice a day orally, the dose amount incrementally increasing from about 400 mg to about 800 mg. In a further embodiment, the amount of HDAC inhibitor administered to the patient ranges from about 0.01 mg/kg to about 50 mg/kg. In yet another embodiment, the HDAC inhibitor is administered to the patient twice a day orally, the dose amount incrementally increasing from about 12 mg/m$^2$ to about 14 mg/m$^2$.

In an aspect of the present invention, the molar ratio of EZH2 inhibitor to HDAC inhibitor may range from about 1:100 to about 100:1, from about 1:80 to about 80:1, from about 1:60 to about 60:1, from about 1:50 to about 50:1, from about 1:40 to about 40:1, from about 1:30 to about 30:1, from about 1:25 to about 25:1, from about 1:20 to about 20:1, from about 1:15 to about 15:1, from about 1:12 to about 12:1, from about 1:10 to about 10:1, from about 1:8 to about 8:1, from about 1:6 to about 6:1, from about 1:5 to about 5:1, from about 1:4 to about 4:1, from about 1:3 to about 3:1, from about 1:2 to about 2:1, or about 1:1.

In one embodiment, the EZH2 inhibitor may be administered to the subject once a day on a 28-day cycle, wherein the cycle repeats for a period of time sufficient for treatment of lymphoma (e.g., from about 12 to 18 months). The HDAC inhibitor may be administered to the subject on days 1, 8, 15 on a 28-day cycle, wherein the cycle repeats for a period of time sufficient for treatment of lymphoma (e.g., from about 12 to 18 months).

In certain embodiments, following a single cycle of administration to the subject, the overall response rate (ORR) of EZH2 inhibitor and HDAC inhibitor reaches at least 25%. Further, following a single cycle of administration to the subject, the ORR of EZH2 inhibitor and HDAC inhibitor achieved in the 3-day, 5-day, 7-day, 14-day, 21-day, 30-day, 1-month, 2-month, 3-month, 4-month, 5-month, or 6-month, period following the administration may be about 1.1 fold, about 1.2 fold, about 1.3 fold, about 1.4 fold, about 1.5 fold, about 1.6 fold, about 1.7 fold, about 1.8 fold, about 1.9 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 8 fold, about 9 fold, about 10 fold, about 12 fold, about 15 fold, about 20 fold, about 25 fold, about 30 fold, about 50 fold, about 100 fold, at least about 1.2 fold, at least about 1.5 fold, at least about 2 fold, at least about 2.5 fold, at least about 3 fold, at least about 3.5 fold, at least about 4 fold, at least about 4.5 fold, at least about 5 fold, at least about 5.5 fold, at least about 6 fold, at least about 6.5 fold, at least about 7 fold, at least about 8 fold, at least about 9 fold, at least about 10 fold, of the sum of the ORR of the EZH2 inhibitor and the ORR of the HDAC inhibitor that would have been achieved in the same period had the dose not been administered in combination.

In an aspect of the present invention, administrating an EZH2 inhibitor and an HDAC inhibitor together provides a synergistic effect measured by Excess Over Bliss value: PEZH2+HDAC=1−(1−PEZH2)*(1−PHDAC).

The EZH2 inhibitor and/or the HDAC inhibitor may be administered orally, intravenously, intramuscularly, topically, arterially, or subcutaneously.

In aspects of the present invention, the patient is a mammal and, in particular, a human.

In aspects of the present invention, the patient tests positive for an EZH2 mutation. In a further aspect, the patient overexpresses EZH2.

In an embodiment, the patient does not manifest a hematologic dose-limiting toxicity during treatment such as neutropenia, febrile neutropenia, thrombocytopenia associated with any clinically important bleeding.

According to the present invention, the lymphoma may be relapsed or refractory lymphoma, B-cell lymphoma, T-cell lymphoma, follicular lymphoma, and double-hit lymphoma.

In an embodiment of the present invention a therapeutically effective amount of pharmaceutical composition comprising an BCL2 inhibitor, an EZH2 inhibitor, and an HDAC inhibitor is administered to a patient in need thereof.

According to the present invention, the EZH2-dysregulated lymphoma includes a gain of function mutation in a gene encoding EZH2. In a further embodiment, the EZH2-dysregulated lymphoma is a germinal cell lymphoma. In another embodiment, wherein the EZH2 inhibitor and the HDAC inhibitor are administered orally.

BRIEF DESCRIPTION OF THE FIGURES

FIGS. 3A-3J. Combination of GSK-126 and Romidepsin leads to Decreased Methylation and Increased Acetylation of H3K27 and Dissociation of PRC2 complex. A. Acetylation of H3K27 is increased after combination therapy as compared to single agent therapy. Tri-methylation is decreased after the combination. B-E. Mass Spectrometry confirms acetylation and methylation findings in 2 germinal center DLBCL cell lines. Fold change calculated relative to control. F. Protein levels of EZH2 and other members of the PRC2 complex are decreased after exposure to GSK126 and romidepsin as compared to single agent therapy. G. Co-immunoprecipitation after treatment with GSK126, romidepsin or the combination demonstrates dissociation of the PRC2 complex members after exposure to the combination of GSK126 and romidepsin. H-I: Mass spectrometry after 24 h exposure to romidepsin (2.5 nM) in SU-DHL-10 cells demonstrates dissociation of EZH2-SUZ12 from the rest of the PRC2 complex. J: Mass spectrometry after co-IP with acetyl lysine antibody demonstrated a 2-fold increase estimated by spectral counts between untreated SU-DHL-10 cells and romidepsin exposed cells. Using Proteome Discoverer 2.1, this acetylated protein was identified as RbAp 46/48 (RBBP4) (FDR<1.0%).

FIGS. 6A-6G. Synergistic Cell Lines Share a Common Basal Gene and Protein Signature. A. Synergistic (EOB≥20) cell lines display a common basal gene expression signature, with upregulated genes such as HDAC9, AHCY, and MBD3. B. 34 of 69 genes identified in the common basal genetic profile amongst synergistic cell lines are found to be altered in primary DLBCL patient samples (cBioPortal, TCGA). C. Synergistic cell lines share enrichment in epigenetic pathways. D, E. Using Meta-VIPER, synergistic cell lines are enriched in pathways involving cell cycle control, DNA replication, and chromatin remodeling with downregulation of differentiation and inflammatory pathways. F. Unbiased interrogation of 400 proteins revealed co-segregation of several proteins with EZH2 including HDAC 1/2 and MYC in primary patient samples (TCGA). G. Protein activity based random forest classifier to predict GSK126 and romidepsin synergy.

FIGS. 8A-8E show synergistic class effect of EZH2 inhibitors in combination with romidepsin in 4 Germinal Center DLBCL Cell Lines. A. 6 day exposure to EPZ011989 in 3 GC-DLBCL cell lines. B. Cell viability curve for Pfeiffer (GC-DLBCL), which demonstrates potent sensitivity to EPZ011989. C. Single agent exposure to CPI-1205 in 4 GC-DLBCL cell lines. D. Co-exposure to EPZ-011989 and romidepsin is synergistic in GC-DLBCL cell lines. E. Pre-treatment for 144 hours (6 days) with CPI-1205 followed by co-Exposure to CPI-1205 and romidepsin is synergistic in GC-DLBCL cell lines. Simultaneous exposure was not as synergistic (not shown).

DETAILED DESCRIPTION

Figure 1A:
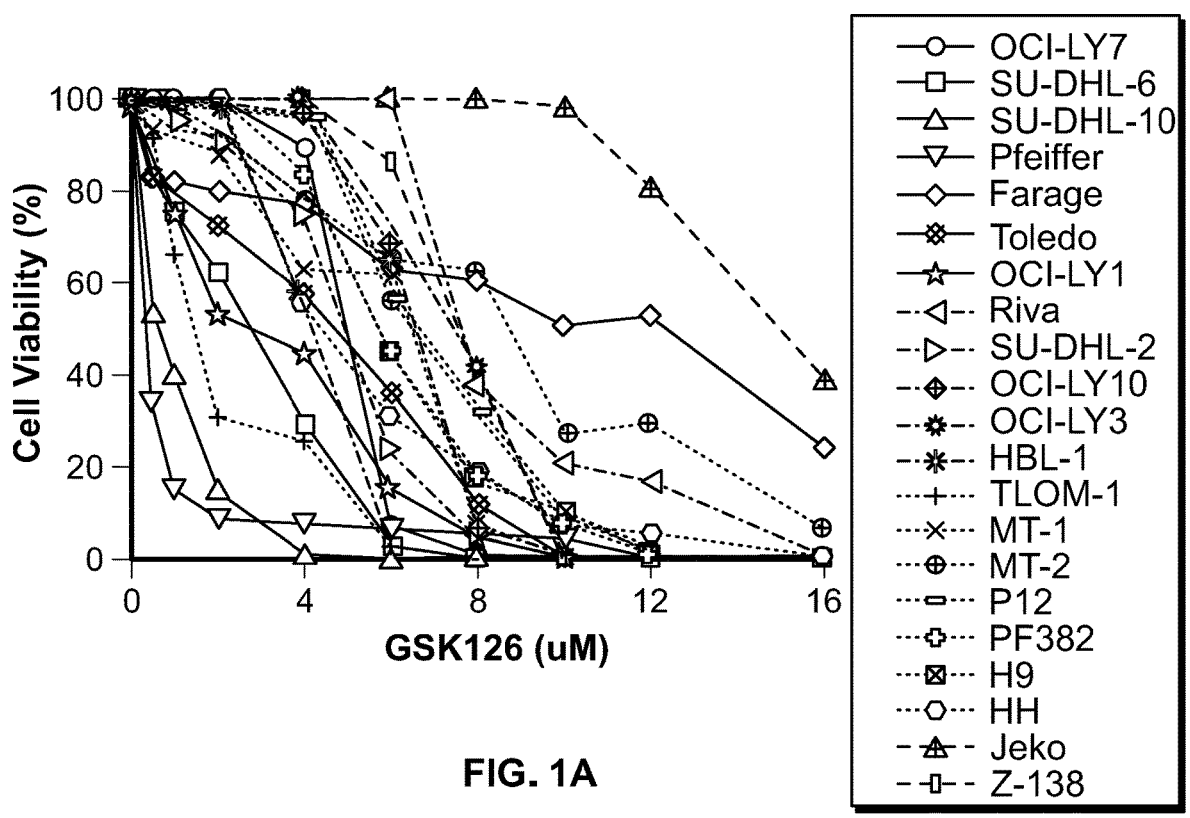
FIGS. 1A-1B. Sensitivity to GSK126 is predicted by the presence of EZH2 mutation. A. Single agent GSK126 cell viability curves of 21 lymphoma cell lines (solid lines: GC-DLBCL, dash-dotted lines: ABC-DLBCL, dotted lines: T cell lymphoma, dashed lines: Mantle cell lymphoma) after 144-hour exposure. B. Cell viability curves for 21 lymphoma cell lines exposed to romidepsin at 72 hours.

The present disclosure provides for methods and compositions for treating cancer. A subject having lymphoma is administered an EZH2 inhibitor and an HDAC inhibitor. The combination of the EZH2 inhibitor and the HDAC inhibitor produces a synergistic effect on the cancer compared to the effect of the EZH2 inhibitor or the HDAC inhibitor alone. For example, the combination may result in a synergistic increase in apoptosis of cancer cells, and/or a synergistic reduction in tumor volume.

The present disclosure provides for a pharmaceutical composition comprising a first amount of an EZH2 inhibitor and a second amount of an HDAC inhibitor. The combination of the first amount of the EZH2 inhibitor and the second amount of the HDAC inhibitor produces a synergistic effect on cancer compared to the effect of the first amount of the EZH2 inhibitor alone or the effect of the second amount of the HDAC inhibitor alone.

The present methods may be used in vitro or in a subject having cancer such as lymphoma.

Any isoform of EZH2 or HDAC may be inhibited by the present inhibitors. The present inhibitors may target the wild-type or mutant EZH2 or HDAC.

Histone deacetylases (HDAC) may be class I, class II (including class IIA, and class IIB), class III, or class IV. HDAC may be HDAC1, HDAC2, HDAC3, HDAC4, HDAC5, HDAC6, HDAC7, HDAC8, HDAC9, HDAC10, HDAC11, sirtuins (e.g., SIRT1, SIRT2, SIRT3, SIRT4, SIRT5, SIRT6, SIRT7), etc.

As used herein, the term "inhibitor" refers to agents capable of down-regulating or otherwise decreasing or suppressing the level/amount and/or activity of EZH2, HDAC or BCL2.

The mechanism of inhibition may be at the genetic level (e.g., interference with or inhibit expression, transcription or translation, etc.) or at the protein level (e.g., binding, competition, etc.).

The present inhibitors (e.g., the EZH2 inhibitor, the HDAC inhibitor, and/or the BCL2 inhibitor) may be a small molecule, a polynucleotide, a polypeptide, or an antibody or antigen-binding portion thereof. In one embodiment, the polynucleotide is a small interfering RNA (siRNA) or an antisense molecule.

In one embodiment, the inhibitor is a CRISPR (clustered regularly interspaced short palindromic repeats)-Cas system specific for EZH2, HDAC or BCL2.

A wide variety of suitable inhibitors may be employed, guided by art-recognized criteria such as efficacy, toxicity, stability, specificity, half-life, etc.

Small Molecule Inhibitors

As used herein, the term "small molecules" encompasses molecules other than proteins or nucleic acids without strict regard to size. Non-limiting examples of small molecules that may be used according to the methods and compositions of the present invention include, small organic molecules, peptide-like molecules, peptidomimetics, carbohydrates, lipids or other organic (carbon containing) or inorganic molecules.

EZH2 is a histone methyltransferase serving as the catalytic subunit of the Polycomb Repression Complex 2 (PRC2), which is responsible for tri-methylation of histone 3 lysine 27 (H3K27me3). EZH2 recruits histone deacetyltransferase (HDAC) 1/2 and DNA methyltransferases (DNMT) through EED to induce additional transcriptional inhibition. Much like Bcl6, EZH2 has been found to have gain of function mutations contributing to lymphomagenesis. In addition, it has been shown that EZH2 and BCL6 cooperate physiologically to enable the germinal center reaction. EZH2 is required for repression of a subset of BCL6 target genes. Given EZH2 dysregulation in several malignancies. EZH2 inhibitors have been developed. EZH2 inhibitors display the most robust activity in cell lines derived from the germinal center.

Tazemetostat is a first-in-class, potent and selective oral inhibitor of EZH2. Phase 1 data demonstrated favorable safety data in patients with relapsed or refractory (R/R) non-Hodgkin's lymphomas and certain genetically defined solid tumors. Activity was studied in a global, multicenter phase 2 study including R/R DLBCL or follicular lymphoma (FL). Patients were prospectively stratified by EZH2 mutational status and cell of origin. Five cohorts were studied: 1) EZH2 mutated GC-DLBCL, (2) GC-DLBCL EZH2 WT, (3) Non-GC-DLBCL, (4) EZH2 mutated FL, and (5) EZH2 wild type FL. Patients were treated with tazemetostat 800 mg BID until progression of disease or withdrawal from study. Preliminary results showed that the therapy was well tolerated with the most common treatment related emergent adverse events including nausea (14%), thrombocytopenia (13%), and anemia (10%). Response rates were highest in patients harboring EZH2 mutations. The overall response rate (ORR) per cohort were as follows: EZH2 MT FL 92%, EZH2 MT DLBCL 29%, EZH2 WT FL 26%, and EZH2 WT DLBCL 15%. The EZH2 WT DLBCL achieved the greatest number of complete responses (8%). There were 17 evaluable patients with EZH2 mutated DLBCL of whom 29% achieved a partial response and 35% achieved stable disease. The median time to first response in the EZH2 MT DLBCL group was 8.3 weeks. In summary, treatment with tazemetostat was safe and led to durable responses, but few complete responses were seen with this single agent target therapy.

Vorinostat, an HDAC inhibitor, was the first epigenetic drug to gain FDA approval, specifically indicated in patients with relapsed/refractory TCL. Two other HDAC inhibitors, romidepsin and belinostat, have gained approval for the treatment of TCL, while panobinostat has been approved for the treatment of relapsed/refractory multiple myeloma. Despite the robust link between epigenetic dysregulation and tumorigenesis in several malignancies, few diseases have demonstrated clinical benefit with single agent epigenetic targeting therapy, including GC-derived B-cell lymphomas.

Non-limiting examples of HDAC inhibitors include, hydroxamic acids (or hydroxamates), such as trichostatin A; cyclic tetrapeptides (such as trapoxin B), and the depsipeptides; benzamides; electrophilic ketones, and the aliphatic acid compounds such as phenylbutyrate and valproic acid. Non-limiting examples of HDAC inhibitors also include, the hydroxamic acids vorinostat (SAHA), belinostat (PXD101), LAQ824, and panobinostat (LBH589); the benzamides: entinostat (MS-275), tacedinaline (CI994), and mocetinostat (MGCD0103); nicotinamide, derivatives of NAD, dihydrocoumarin, naphthopyranone, and 2-hydroxynaphthaldehydes.

In certain embodiments, the inhibitor used in the present methods and compositions is a polynucleotide that reduces expression of EZH2 or HDAC.

The nucleic acid target of the polynucleotides (e.g., siRNA, antisense oligonucleotides, and ribozymes) may be any location within the gene or transcript of EZH2 or HDAC.

RNA Interference

SiRNAs (small interfering RNAs) or small-hairpin RNA (shRNA) may be used to reduce the level of EZH2 or HDAC.

SiRNAs may have 16-30 nucleotides, e.g., 16, 17, 18, 19, 20, 21, 22, 23, 24, 25, 26, 27, 28, 29, or 30 nucleotides. The siRNAs may have fewer than 16 or more than 30 nucleotides. The polynucleotides of the invention include both unmodified siRNAs and modified siRNAs such as siRNA derivatives etc.

SiRNAs can be delivered into cells in vitro or in vivo by methods known in the art, including cationic liposome transfection and electroporation. SiRNAs and shRNA molecules can be delivered to cells using viruses or DNA vectors.

Antisense Polynucleotides

In other embodiments, the polynucleotide of the invention is an antisense nucleic acid sequence that is complementary to a target region within the mRNA of EZH2 or HDAC. The antisense polynucleotide may bind to the target region and inhibit translation. The antisense oligonucleotide may be DNA or RNA, or comprise synthetic analogs of ribo-deoxynucleotides. Thus, the antisense oligonucleotide inhibits expression of EZH2 or HDAC.

An antisense oligonucleotide can be, for example, about 7, 10, 15, 20, 25, 30, 35, 40, 45, 50, 55, 60, 65, 70, 75, 80, or more nucleotides in length.

The antisense nucleic acid molecules of the invention may be administered to a subject, or generated in situ such that they hybridize with or bind to the mRNA of EZH2 or HDAC. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using viruses or DNA vectors.

Ribozyme

In other embodiments, the polynucleotide of the invention is a ribozyme that inhibits expression of the gene of EZH2 or HDAC.

Ribozymes can be chemically synthesized in the laboratory and structurally modified to increase their stability and catalytic activity using methods known in the art. Alternatively, ribozyme encoding nucleotide sequences can be introduced into host cells through gene-delivery mechanisms known in the art.

Other aspects of the invention include vectors (e.g., viral vectors, expression cassettes, plasmids) comprising or encoding polynucleotides of the subject invention (e.g., siRNA, antisense nucleic acids, and ribozymes), and host cells genetically modified with polynucleotides or vectors of the subject invention.

Polypeptides

The present inhibitors can also be a polypeptide exhibiting inhibitory activity toward EZH2 or HDAC.

Various means for delivering polypeptides to a cell can be utilized to carry out the methods of the subject invention. For example, protein transduction domains (PTDs) can be fused to the polypeptide, producing a fusion polypeptide, in which the PTDs are capable of transducing the polypeptide cargo across the plasma membrane (Wadia, J. S. and Dowdy, S. F., Curr. Opin. Biotechnol., 2002, 13(1)52-56).

According to the methods of the subject invention, recombinant cells can be administered to a patient, wherein the recombinant cells have been genetically modified to express a nucleotide sequence encoding an inhibitory polypeptide.

Antibodies

The present inhibitors can be an antibody or antigen-binding portion thereof that is specific to EZH2 or HDAC.

The antibody or antigen-binding portion thereof may be the following: (a) a whole immunoglobulin molecule; (b) an scFv; (c) a Fab fragment; (d) an F(ab')2; and (e) a disulfide linked Fv. The antibody or antigen-binding portion thereof may be monoclonal, polyclonal, chimeric and humanized. The antibodies may be murine, rabbit or human antibodies.

Combination Therapy

The present method for treating cancer may comprise the step of administering to a subject an EZH2 inhibitor and an HDAC inhibitor.

This may be achieved by administering a pharmaceutical composition that includes both agents (an EZH2 inhibitor and an HDAC inhibitor), or by administering two pharmaceutical compositions, at the same time or within a short time period, wherein one composition comprises an EZH2 inhibitor, and the other composition includes an HDAC inhibitor.

The combination of an EZH2 inhibitor and an HDAC inhibitor produces an additive or synergistic effect (i.e., greater than additive effect) in treating the cancer compared to the effect of the EZH2 inhibitor or the HDAC inhibitor alone. For example, the combination may result in a synergistic increase in apoptosis of cancer cells, and/or a synergistic reduction in tumor volume. In different embodiments, depending on the combination and the effective amounts used, the combination of compounds can inhibit tumor growth, achieve tumor stasis, or achieve substantial or complete tumor regression.

In various embodiments, the present invention provides methods to reduce cancer cell growth, proliferation, and/or metastasis, as measured according to routine techniques in the diagnostic art. Specific examples of relevant responses include reduced size, mass, or volume of a tumor, or reduction in cancer cell number.

The present compositions and methods can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; preventing, inhibiting or ameliorating the cancer in the subject, such as slowing progression of the cancer, reducing or ameliorating a sign or symptom of the cancer; reducing the rate of tumor growth in a patient; preventing the continued growth of a tumor, reducing the size of a tumor; and/or disappearance of markers associated with undesirable, unwanted, or aberrant cell proliferation.

Methods and compositions of the present invention can be used for prophylaxis as well as amelioration of signs and/or symptoms of cancer.

In some embodiments, the combination therapy results in a synergistic effect, for example, the EZH2 inhibitor and the HDAC inhibitor act synergistically, for example, in the apoptosis of cancer cells, inhibition of proliferation/survival of cancer cells, in the production of tumor stasis.

In certain embodiments, the term "synergy" may refer to a greater than additive effect as measured by an Excess Over Bliss (EOB).

In one embodiment, EOB evaluates if the combined effect of two compounds is significantly greater or smaller than the combination of their individual (independent) effects. EOB may be measured by calculating the difference between the observed and predicted inhibition of the drug combination. For two single compounds with inhibition effects A and B, the predicted inhibition for the drug combination, C, is calculated as $C=A+B-A*B$, where A and B are fractional growth inhibitions of drugs A and B at a given dosage. Each effect may be expressed as fractional inhibition between 0 and 1. The excess over Bliss (EOB) is the difference between the predicted inhibition C and the observed growth inhibition of the combination of A and B at the same dosage. The EOB may be calculated by subtracting the predicted Bliss effect C from the experimentally observed inhibition at each pair of concentrations. EOB values for three or more drug combinations can be calculated similarly. Borisy A A, Elliott P J, Hurst N W, et al. Systematic discovery of multicomponent therapeutics. Proceedings of the National Academy of Sciences of the United States of America, 2003; 100:7977-82; Berenbaum M C. Criteria for analyzing interactions between biologically active agents. Advances in cancer research 1981; 35:269-335.

In one embodiment, $EOB \geq 0$ indicates an additive or synergistic effect, and minus score (<0) indicates an antagonistic effect. In another embodiment, an EOB value of about 0 indicates an additive effect, whereas positive EOB values indicate synergistic effects. In one embodiment, Excess over Bliss$\geq 20$ indicates strongly synergistic and EOB$\leq -20$ indicates strongly antagonistic.

The EOB of the present combination of agents (e.g., a combination of an EZH2 inhibitor and an HDAC inhibitor, or a combination of a BCL2 inhibitor, an EZH2 inhibitor, and an HDAC inhibitor) may be greater than about 2, greater than (or less than) about 3, greater than (or less than) about 4, greater than (or less than) about 5, greater than (or less than) about 6, greater than (or less than) about 7, greater than (or less than) about 8, greater than (or less than) about 9, greater than (or less than) about 10, greater than (or less than) about 11, greater than (or less than) about 12, greater than (or less than) about 13, greater than (or less than) about 14, greater than (or less than) about 15, greater than (or less than) about 16, greater than (or less than) about 17, greater than (or less than) about 18, greater than (or less than) about 19, greater than (or less than) about 20, greater than (or less than) about 21, greater than (or less than) about 22, greater than (or less than) about 23, greater than (or less than) about 24, greater than (or less than) about 25, greater than (or less than) about 26, greater than (or less than) about 27, greater than (or less than) about 28, greater than (or less than) about 29, greater than (or less than) about 30, greater than (or less than) about 31, greater than (or less than) about 32, greater than (or less than) about 33, greater than (or less than) about 34, greater than (or less than) about 35, greater than (or less than) about 36, greater than (or less than) about 37, greater than (or less than) about 38, greater than (or less than) about 39, greater than (or less than) about 40, greater than (or less than) about 41, greater than (or less than) about 42, greater than (or less than) about 43, greater than (or less than) about 44, greater than (or less than) about 45, greater than (or less than) about 46, greater than (or less than) about 47, greater than (or less than) about 48, greater than (or less than) about 49, greater than (or less than) about 50, greater than (or less than) about 51, greater than (or less than) about 52, greater than (or less than) about 53, greater than (or less than) about 54, greater than (or less than) about 55, greater than (or less than) about 56, greater than (or less than) about 57, greater than (or less than) about 58, greater than (or less than) about 59, or greater than (or less than) about 60.

In some embodiments, the combination therapy results in a synergistic effect, for example, the EZH2 inhibitor and the HDAC inhibitor (or a combination of a BCL2 inhibitor, an EZH2 inhibitor, and an HDAC inhibitor) act synergistically, for example, in the apoptosis of cancer cells, inhibition of proliferation/survival of cancer cells, in the production of tumor stasis.

As used herein, the term "synergy" (or "synergistic") means that the effect achieved with the methods and combinations of the present disclosure is greater than the sum of the effects that result from using the individual agents alone, e.g., using the EZH2 inhibitor alone and the HDAC inhibitor alone. For example, the effect (e.g., apoptosis of cells, a decrease in cell viability, cytotoxicity, a decrease in cell proliferation, a decrease in cell survival, inhibition of tumor growth, a reduction in tumor volume, and/or tumor stasis, etc. as described herein) achieved with the combination of an EZH2 inhibitor and an HDAC inhibitor (or a combination of a BCL2 inhibitor, an EZH2 inhibitor, and an HDAC inhibitor) is about 1.1 fold, about 1.2 fold, about 1.3 fold, about 1.4 fold, about 1.5 fold, about 1.6 fold, about 1.7 fold, about 1.8 fold, about 1.9 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 8 fold, about 9 fold, about 10 fold, about 12 fold, about 15 fold, about 20 fold, about 25 fold, about 30 fold, about 50 fold, about 100 fold, at least about 1.2 fold, at least about 1.5 fold, at least about 2 fold, at least about 2.5 fold, at least about 3 fold, at least about 3.5 fold, at least about 4 fold, at least about 4.5 fold, at least about 5 fold, at least about 5.5 fold, at least about 6 fold, at least about 6.5 fold, at least about 7 fold, at least about 8 fold, at least about 9 fold, at least about 10 fold, of the sum of the effects that result from using the EZH2 inhibitor alone and the HDAC inhibitor alone.

Synergistic effects of the combination may also be evidenced by additional, novel effects that do not occur when either agent is administered alone, or by reduction of adverse side effects when either agent is administered alone.

Cytotoxicity effects can be determined by any suitable assay, including, but not limited to, assessing cell membrane integrity (using, e.g., dyes such as trypan blue or propidium iodide, or using lactate dehydrogenase (LDH) assay), measuring enzyme activity, measuring cell adherence, measuring ATP production, measuring co-enzyme production, measuring nucleotide uptake activity, crystal violet method, Tritium-labeled Thymidine uptake method, measuring lactate dehydrogenase (LDH) activity, 3-(4,5-Dimethyl-2-thiazolyl)-2,5-diphenyl-2H-tetrazolium bromide (MTT) or MTS assay, sulforhodamine B (SRB) assay, WST assay, clonogenic assay, cell number count, monitoring cell growth, etc.

Apoptosis of cells may be assayed by any suitable method, including, but not limited to, TUNEL (terminal deoxynucleotidyl transferase dUTP nick end labeling) assay, assaying levels of cytochrome C release, assaying levels of cleaved/activated caspases, assaying 5-bromo-2'-deoxyuridine labeled fragmented DNA, assaying levels of survivin etc.

Other methods that can be used to show the synergistic effects of the present methods, pharmaceutical compositions and combinations include, but are not limited to, clonogenic assay (colony formation assay) to show decrease in cell survival and/or proliferation, studying tumor volume reduction in animal models (such as in mice, etc.)

In one embodiment, advantageously, such synergy provides greater efficacy at the same doses, lower side effects, and/or prevents or delays the build-up of multi-drug resistance.

The EZH2 inhibitor and the HDAC inhibitor may be administered simultaneously, separately or sequentially. They may exert an advantageously combined effect (e.g., additive or synergistic effects).

For sequential administration, either an EZH2 inhibitor is administered first and then an HDAC inhibitor, or the HDAC inhibitor is administered first and then an EZH2 inhibitor. In embodiments where an EZH2 inhibitor and an HDAC inhibitor are administered separately, administration of a first agent can precede administration of a second agent by seconds, minutes, hours, days, or weeks. The time difference in non-simultaneous administrations may be greater than 1 minute, and can be, for example, precisely, at least, up to, or less than 5 minutes, 10 minutes, 15 minutes, 30 minutes, 45 minutes, 60 minutes, 2 hours, 3 hours, 6 hours, 9 hours, 12 hours, 24 hours, 36 hours, or 48 hours, or more than 48 hours. The two or more agents can be administered within minutes of each other or within about 0.5, about 1, about 2, about 3, about 4, about 6, about 9, about 12, about 15, about 18, about 24, or about 36 hours of each other or within about 1, 2, 3, 4, 5, 6, 7, 8, 9, 10, 12, 14 days of each other or within about 2, 3, 4, 5, 6, 7, 8, 9, or 10 weeks of each other. In some cases, longer intervals are possible.

The present invention also provides for a pharmaceutical composition comprising (i) an EZH2 inhibitor; (ii) an HDAC inhibitor; and (iii) at least one pharmaceutically acceptable excipient.

The present method for treating GC-DLBCL may be achieved by administering a pharmaceutical composition that includes both agents (an EZH2 inhibitor and an HDAC inhibitor), or by administering two pharmaceutical compositions, one containing an EZH2 inhibitor and one containing an HDAC inhibitor, at the same time or within a short time period. For sequential administration, the EZH2 inhibitor may be administered before the HDAC inhibitor or the HDAC inhibitor may be administered before the EZH2 inhibitor.

In some embodiments, the subject is a human subject having a hematopoietic malignancy. As used herein a hematopoietic malignancy refers to a malignant abnormality involving hematopoietic cells (e.g., blood cells, including progenitor and stem cells). Examples of hematopoietic malignancies include, without limitation, lymphoma, leukemia, or multiple myeloma. Leukemias include acute myeloid leukemia, acute lymphoid leukemia, chronic myelogenous leukemia, acute lymphoblastic leukemia or chronic lymphoblastic leukemia, and chronic lymphoid leukemia.

The present method may be used to treat lymphoma. Non-limiting examples of lymphoma include, Hodgkin's lymphoma, non-Hodgkin's lymphoma, multiple myeloma, and immunoproliferative diseases (e.g., Epstein-Barr virus-associated lymphoproliferative diseases). Non-limiting examples of lymphoma also include, relapsed or refractory lymphoma, B-cell lymphoma, T-cell lymphoma, follicular lymphoma, double-hit lymphoma, mature B cell neoplasms, mature T cell and natural killer (NK) cell neoplasms, precursor lymphoid neoplasms, immunodeficiency-associated lymphoproliferative disorders, small lymphocytic lymphoma, Burkitt's lymphoma, etc. The lymphoma may be low-grade lymphomas, intermediate-grade lymphomas, high-grade lymphomas, low-grade lymphomas.

Alternatively or in addition, the methods described herein may be used to treat non-hematopoietic cancers, including without limitation, lung cancer, ear, nose and throat cancer, colon cancer, melanoma, pancreatic cancer, mammary cancer, prostate cancer, breast cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; liver cancer; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Carcinomas are cancers of epithelial origin. Carcinomas intended for treatment with the methods of the present disclosure include, but are not limited to, acinar carcinoma, acinous carcinoma, alveolar adenocarcinoma (also called adenocystic carcinoma, adenomyoepithelioina, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Huirthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the present disclosure are used to treat subjects having cancer of the breast, cervix, ovary, prostate, lung, colon and rectum, pancreas, stomach or kidney.

Sarcomas are mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone) Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

Pharmaceutical Compositions

An EZH2 inhibitor and/or an HDAC inhibitor of the present invention may be present in a pharmaceutical composition in an amount ranging from about 0.005% (w/w) to about 100% (w/w), from about 0.01% (w/w) to about 90% (w/w), from about 0.1% (w/w) to about 80% (w/w), from about 1% (w/w) to about 70% (w/w), from about 10% (w/w) to about 60% (w/w), from about 0.01% (w/w) to about 15% (w/w), or from about 0.1% (w/w) to about 20% (w/w) of the total weight of the pharmaceutical composition.

An EZH2 inhibitor and/or an HDAC inhibitor of the present invention may be present in two separate pharmaceutical compositions to be used in a combination therapy.

The agents or pharmaceutical compositions of the present invention may be administered by any route, including, without limitation, oral, transdermal, ocular, intraperitoneal, intravenous, ICV, intracisternal injection or infusion, subcutaneous, implant, sublingual, subcutaneous, intramuscular, intravenous, rectal, mucosal, ophthalmic, intrathecal, intra-articular, intra-arterial, sub-arachnoid, bronchial and lymphatic administration. The present composition may be administered parenterally or systemically.

The pharmaceutical compositions of the present invention can be, e.g., in a solid, semi-solid, or liquid formulation. Intranasal formulation can be delivered as a spray or in a drop; inhalation formulation can be delivered using a nebulizer or similar device; topical formulation may be in the form of gel, ointment, paste, lotion, cream, poultice, cataplasm, plaster, dermal patch aerosol, etc.; transdermal formulation may be administered via a transdermal patch or iontorphoresis. Compositions can also take the form of tablets, pills, capsules, semisolids, powders, sustained release formulations, solutions, emulsions, suspensions, elixirs, aerosols, chewing bars or any other appropriate compositions.

The composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed release bolus, or continuous administration.

To prepare such pharmaceutical compositions, one or more of compound of the present invention may be mixed with a pharmaceutical acceptable excipient, e.g., a carrier, adjuvant and/or diluent, according to conventional pharmaceutical compounding techniques.

Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers, preservatives and adjuvants, see Remington's Pharmaceutical Sciences, edited by E. W. Martin (Mack Publishing Company, 18th ed., 1990). Additional excipients, for example sweetening, flavoring and coloring agents, may also be present.

The pharmaceutically acceptable excipient may be selected from the group consisting of fillers, e.g. sugars and/or sugar alcohols, e.g. lactose, sorbitol, mannitol, maltodextrin, etc.; surfactants, e.g. sodium lauryle sulfate, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants. Pharmaceutically acceptable carriers include any and all clinically useful solvents, dispersion media, coatings, antibacterial and antifungal agents, isotonic and absorption delaying agents and the like.

The pharmaceutical composition may contain excipients for modifying, maintaining or preserving, for example, the pH, osmolarity, viscosity, clarity, color, isotonicity, odor, sterility, stability, rate of dissolution or release, adsorption or penetration of the composition. Suitable excipients include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris HCl, citrates, phosphates, other organic acids); bulking agents (such as mannitol or glycine), chelating agents (such as ethylenediamine tetraacetic acid (EDTA), ethylene glycol tetraacetic acid (EGTA)); complexing agents (such as caffeine, polyvinylpyrrolidone, beta cyclodextrin or hydroxypropyl beta cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (in one aspect, sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

Oral dosage forms may be tablets, capsules, bars, sachets, granules, syrups and aqueous or oily suspensions. Tablets may be formed form a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound, may be prepared by known methods. The contents of the capsule may be formulated using known methods so as to give sustained release of the active compounds. Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example *arachis* oil. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium. U.S. Pat. No. 8,263,662.

Intravenous forms include, but are not limited to, bolus and drip injections. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

Additional compositions include formulations in sustained or controlled delivery, such as using liposome or micelle carriers, bioerodible microparticles or porous beads and depot injections.

The present compound(s) or composition may be administered as a single dose, or as two or more doses (which may or may not contain the same amount of the desired molecule) over time, or as a continuous infusion via implantation device or catheter. The pharmaceutical composition can be prepared in single unit dosage forms.

Appropriate frequency of administration can be determined by one of skill in the art and can be administered once or several times per day (e.g., twice, three, four or five times daily). The compositions of the invention may also be administered once each day or once every other day. The compositions may also be given twice weekly, weekly, monthly, or semi-annually. In the case of acute administration, treatment is typically carried out for periods of hours or days, while chronic treatment can be carried out for weeks, months, or even years. U.S. Pat. No. 8,501,686.

Administration of the compositions of the invention can be carried out using any of several standard methods including, but not limited to, continuous infusion, bolus injection, intermittent infusion, inhalation, or combinations of these methods. For example, one mode of administration that can be used involves continuous intravenous infusion. The infusion of the compositions of the invention can, if desired, be preceded by a bolus injection.

As used herein, the term "therapeutically effective amount" is an amount sufficient to treat a specified disorder or disease or alternatively to obtain a pharmacological response treating a disorder or disease.

Methods of determining the most effective means and dosage of administration can vary with the composition used for therapy, the purpose of the therapy, the target cell being treated, and the subject or patient being treated. Single or multiple administrations can be carried out with the dose level and pattern being selected by the treating physician. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

For example, an EZH2 inhibitor and/or an HDAC inhibitor may be administered at about 0.0001 mg/kg to about 500 mg/kg, about 0.01 mg/kg to about 200 mg/kg, about 0.01 mg/kg to about 0.1 mg/kg, about 0.1 mg/kg to about 100 mg/kg, about 10 mg/kg to about 200 mg/kg, about 10 mg/kg to about 20 mg/kg, about 5 mg/kg to about 15 mg/kg, about 0.0001 mg/kg to about 0.001 mg/kg, about 0.001 mg/kg to about 0.01 mg/kg, about 0.01 mg/kg to about 0.1 mg/kg, about 0.1 mg/kg to about 0.5 mg/kg, about 0.5 mg/kg to about 1 mg/kg, about 1 mg/kg to about 2.5 mg/kg, about 2.5 mg/kg to about 10 mg/kg, about 10 mg/kg to about 50 mg/kg, about 50 mg/kg to about 100 mg/kg, about 100 mg/kg to about 250 mg/kg, about 0.1 µg/kg to about 800 µg/kg, about 0.5 µg/kg to about 500 µg/kg, about 1 µg/kg to about 20 µg/kg, about 1 µg/kg to about 10 µg/kg, about 10 µg/kg to about 20 µg/kg, about 20 µg/kg to about 40 µg/kg, about 40 µg/kg to about 60 µg/kg, about 60 µg/kg to about 100 µg/kg, about 100 µg/kg to about 200 µg/kg, about 200 µg/kg to about 300 µg/kg, or about 400 µg/kg to about 600 µg/kg. In some embodiments, the dose is within the range of about 250 mg/kg to about 500 mg/kg, about 0.5 mg/kg to about 50 mg/kg, or any other suitable amounts.

The effective amount of the EZH2 inhibitor and/or HDAC inhibitor of the present invention for the combination therapy may be less than, equal to, or greater than when the agent is used alone.

The amount or dose of an EZH2 inhibitor and/or an HDAC inhibitor of the present invention may range from about 0.01 mg to about 10 g, from about 0.1 mg to about 9 g, from about 1 mg to about 8 g, from about 1 mg to about 7 g, from about 5 mg to about 6 g, from about 10 mg to about 5 g, from about 20 mg to about 1 g, from about 50 mg to about 800 mg, from about 100 mg to about 500 mg, from about 600 mg to about 800 mg, from about 800 mg to about 1 g, from about 0.01 mg to about 10 g, from about 0.05 µg to about 1.5 mg, from about 10 µg to about 1 mg protein, from about 0.1 mg to about 10 mg, from about 2 mg to about 5 mg, from about 1 mg to about 20 mg, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg.

Different dosage regimens may be used. In some embodiments, a daily dosage, such as any of the exemplary dosages described above, is administered once, twice, three times, or four times a day for at least three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

Non-limiting examples of dosage regimens according to the present invention include:

TABLE 1

| Dose Cohort | Tazemetostat PO BID Days 1-28 | Romidepsin IV over 4 hours Days 1, 8, 15 |
| --- | --- | --- |
| Level −1 | 400 mg | 10 mg/m$^2$ |
| Level 1 | 400 mg | 12 mg/m$^2$ |
| Level 2 | 800 mg | 12 mg/m$^2$ |
| Level 3 | 800 mg | 14 mg/m$^2$ |
| | | 28 Day Cycle |
| | | Patients may receive antiemetics prior to romidepsin |

Kits

The present disclosure also provides for a kit for use in the treatment or prevention of cancer or other conditions. Kits according to the present disclosure include package(s) (e.g., vessels) comprising the present agents or compositions. The kit may include (i) an EZH2 inhibitor, and (ii) an HDAC inhibitor. The EZH2 inhibitor and the HDAC inhibitor may be present in the pharmaceutical compositions as described herein. The EZH2 inhibitor and the HDAC inhibitor may be present in unit dosage forms.

Examples of pharmaceutical packaging materials include, but are not limited to, bottles, tubes, inhalers, pumps, bags, vials, containers, syringes, bottles, and any packaging material suitable for a selected formulation and intended mode of administration and treatment.

Kits can contain instructions for administering the present agents or compositions to a patient. Kits also can comprise instructions for uses of the present agents or compositions. Kits also can contain labeling or product inserts for the agents/compositions. The kits also can include buffers for preparing solutions for conducting the methods. The instruction of the kits may state that the combination of the EZH2 inhibitor and the HDAC inhibitor produces a synergistic effect on the cancer (e.g., lymphoma) compared to the effect of the EZH2 inhibitor alone or the effect of the HDAC inhibitor alone.

Subjects, which may be treated according to the present invention include all animals which may benefit from administration of the agents of the present invention. Such subjects include mammals, preferably humans, but can also be an animal such as dogs and cats, farm animals such as cows, pigs, sheep, horses, goats and the like, and laboratory animals (e.g., rats, mice, guinea pigs, and the like).

The following are examples of the present invention and are not to be construed as limiting.

EXAMPLES

Example 1—GSK126 and Romidepsin are Synergistic

The findings of this study include the following. EZH2 and HDAC inhibition synergistically modulates histone acetylation and methylation in preclinical models of EZH2 dysregulated lymphomas. Synergistic effects of combined EZH2 and HDAC inhibition may be predicted by a basal gene expression and protein signature.

Enhancer of zeste homolog 2 (EZH2) is the catalytic subunit of the Polycomb Repressor Complex 2 and induces trimethylation of histone 3 lysine 27 (H3K27), a mark of transcriptional repression. With the discovery of activating mutations, EZH2 has been implicated in the pathogenesis of germinal center (GC) derived lymphomas. Inactivating mutations in CBP and EP300, histone acetyltransferases, are also common in GC-derived lymphomas, and acetylation can be indirectly modulated by HDAC inhibitors. Exposure to GSK126, an EZH2 inhibitor, and romidepsin, a pan-HDAC inhibitor, demonstrated potent synergy in lymphoma cell lines with EZH2 dysregulation. Combination of romidepsin with other EZH2 inhibitors also demonstrated synergy suggesting that the combination of EZH2 inhibition and romidepsin is a class effect of EZH2. Dual inhibition of EZH2 and HDAC leads to modulation of acetylation and methylation of H3K27. The synergistic effects of simultaneous inhibition of EZH2 and HDAC may be due to disruption of the PRC2 complex secondary to acetylation of RbAP 46/48. A common basal gene signature is shared among synergistic lymphoma cell lines and are characterized by upregulation in chromatin remodeling genes and transcriptional regulators. This finding was supported by metaVIPER analysis which also revealed that HDAC 1/2 and DNMT are strongly associated with EZH2 activation. Our findings support combination of EZH2 and HDAC inhibition in EZH2 dysregulated lymphomas.

Our group and others have established a proof-of-principle for selective targeting of epigenetic modifiers in DLBCL. The combination of niacinamide, a sirtuin inhibitor, and pan-HDACis, including romidepsin, are synergistic in GC-DLBCL and leads to abrogation of BCL6 and activation of p53 through acetylation[18]. A phase I clinical study utilizing vorinostat and niacinamide in relapsed/refractory lymphoma demonstrated an ORR of 24% suggesting a potential role for combination epigenetic therapy in B-cell lymphomas. The combination of panobinostat and decitabine, a DNA Methyltransferase inhibitor (DNMTi), was found to be more synergistic in GC-DLBCL compared to Activated B-Cell (ABC) DLBCL cell lines leading to a unique differential expression of various genes including SMAD1 and DNMT3A[19]. Taken together, although single agent epigenetic therapy has been disappointing in DLBCL, the aforementioned data supports a platform based on a combination of epigenetic targeted agents as a therapeutic method for the treatment of GC-DLBCL.

Given the frequent dysfunction of EZH2 as well as HATs in GC-derived B-cell lymphomas, we hypothesized that the rationale combination of EZH2 and HDAC inhibitors will be synergistic by modulating both acetylation and methylation states, in turn, triggering apoptosis. To our knowledge, there are no studies combining EZH2 inhibitors in conjunction with clinically available epigenetic targeting drugs. Herein, we demonstrate that GSK126, an EZH2 inhibitor, and romidepsin, a pan-HDAC inhibitor, were synergistic by disrupting the PRC2 complex, modulating histone acetylation and methylation. Furthermore, we present that the sensitivity to this combination is associated with a specific gene expression signature.

This experiment demonstrated that GSK126, an EZH2 inhibitor, and romidepsin, a pan-HDAC inhibitor, were synergistic, disrupted the PRC2 complex, and modulated histone acetylation and methylation. Furthermore, the sensitivity to this combination was associated with a specific gene expression signature.

Material and Methods

Cell Lines and Culture

OCI-LY1, SU-DHL-2, SU-DHL-6, Pfeiffer, Farage, Toledo, Riva, HBL-1, Jeko-1, Z-138, H9, and HH were obtained from ATCC. OCI-LY7, OCI-LY10, SU-DHL-10 and OCI-LY3 were obtained from DSMZ. PF382, and P12 were a gift from the laboratory of Adolfo Fernando. TLOM-1 and MT-1 were obtained from Kyoto University; and MT-2 was obtained from Memorial Sloan Kettering Cancer Center. All cell lines were authenticated and screened for mycoplasma using the ATCC/Promega STR Authentication Testing Kit and Lonza MycoAlert.

Cell Viability Assays

Cells were counted and re-suspended based on their optimal density for log-phase growth. Cell viability and cytotoxicity assays were performed as previously described18-20. Cells were exposed to romidepsin (Selleckchem), ACY957 (Acetylon), GSK126 (Selleckchem), EPZ-011989 (Epizyme), and CPI-1205 (Selleckchem). Synergy was assessed by excess over bliss (EOB). Borisy A A, Elliott P J, Hurst N W, et al. Systematic discovery of multicomponent therapeutics. Proceedings of the National Academy of Sciences of the United States of America, 2003; 100:7977-82; Berenbaum M C. Criteria for analyzing interactions between biologically active agents. Advances in cancer research 1981; 35:269-335. Sensitivity to GSK126 and romidepsin as determined by mean IC50 was correlated with EZH2 mutation/overexpression and HAT mutations, respectively, using Prism GraphPad's student paired t-test.

Flow Cytometry

Flow cytometry analysis was performed using FITC Annexin V Apoptosis Detection Kit with PI (Biolegend #640194) as previously described. Paoluzzi L, Gonen M, Gardner J R, et al. Targeting Bcl-2 family members with the BH3 mimetic AT-101 markedly enhances the therapeutic effects of chemotherapeutic agents in in vitro and in vivo models of B-cell lymphoma. Blood 2008; 111:5350-8.

Co-Immunoprecipitation

Immunoprecipitation was performed using the Pierce™ Co-Immunoprecipitation Kit (#26149). Columns were prepared with 20 to 40 ug of antibody. Whole Protein lysate was incubated with antibody. Flow through was collected and column was washed and eluted. Antibodies used were: anti-EZH2 (Cell Signaling Technology), anti-SUZ12 (Cell Signaling Technology), anti-RbAP 46/48 (Cell Signaling Technology), anti-EED (Millipore), anti-HDAC2 (Cell Signaling Technology), anti-DNMT3L (Novus Biologicals).

Western Blotting

Western blotting was performed as previously described. Amengual J E, Clark-Garvey S, Kalac M, et al. Sirtuin and pan-class I/II deacetylase (DAC) inhibition is synergistic in preclinical models and clinical studies of lymphoma. Blood 2013; 122:2104-13; Kalac M, Scotto L, Marchi E, et al. HDAC inhibitors and decitabine are highly synergistic and associated with unique gene-expression and epigenetic profiles in models of DLBCL. Blood 2011; 118:5506-16.

Mass Spectrometry for Acetylation of PRC2 Complex

Immunoprecipitation was performed using Thermo Scientific™ Pierce™ MS-Compatible Magnetic IP Kit (#84840). Protein was incubated with EZH2 or acetylated-lysine antibody. Antibody bound proteins were eluted and run into SDS PAGE. The excised gel lane pieces were reduced, alkylated, and digested in Trypsin Gold (Promega) digestion buffer (Thermo Fischer Scientific). Condensed evaporated water was collected by brief centrifugation using microcentrifuge (Eppendorf). The gel pieces and digestion reaction were mixed with 2.5% Trifluoretic Acids (TFA, Thermo Fischer Scientific). Peptides were extracted with 70% acetonitrile (ACN/5% TFA mixture) (Thermo Fischer Scientific). The extracts were pooled and dried to completion in SpeedVac.

The concentrated peptide mix was reconstituted in a solution of 2% ACN, 2% formic acid (FA) for MS analysis. Peptides were eluted from the column using a Dionex Ultimate 3000 Nano LC system. Using Thermo Fusion Tribrid mass spectrometer (Thermo Scientific), eluted peptides were electro sprayed. Mass spectrometer-scanning functions and HPLC gradients were controlled by the Xcalibur data system (Thermo Fischer).

Database Search and Interpretation of MS/MS Data

Tandem mass spectra from raw files were searched against uniprot_human_170129.fasta data base using the Proteome Discoverer 2.1 (Thermo Fischer). The mouse protein database was downloaded as FASTA-formatted sequences from Uniprot protein database (January 2017). The peptide mass search tolerance was 10 ppm. A minimum sequence length of 7 amino acids residues was required. To calculate confidence levels and false positive rates (FDR), Proteome Discoverer generates a decoy database and performs the search against this concatenated database (non-decoy+decoy). Scaffold (Proteome Software, Inc) was used to visualize and filter to <1% FDR at the protein level. Spectral counts were used for estimation of relative protein abundance.

HDAC shRNA

Human HDAC2 shRNA plasmids were purchased from Origene (#TG312495). HEK293 cells were plated in OPTI-MEM containing shRNA or scramble using Lipofectamine 3000 (Cat #L3000075). Cells were selected with puromycin, continuously cultured in the presence of puromycin and periodically analyzed by flow cytometry and fluorescent microscopy to monitor GFP levels until a stable cell line had been generated.

Results

GSK126 and Romidepsin Synergize in EZH2 Dysregulated Lymphomas

Figure 1B:
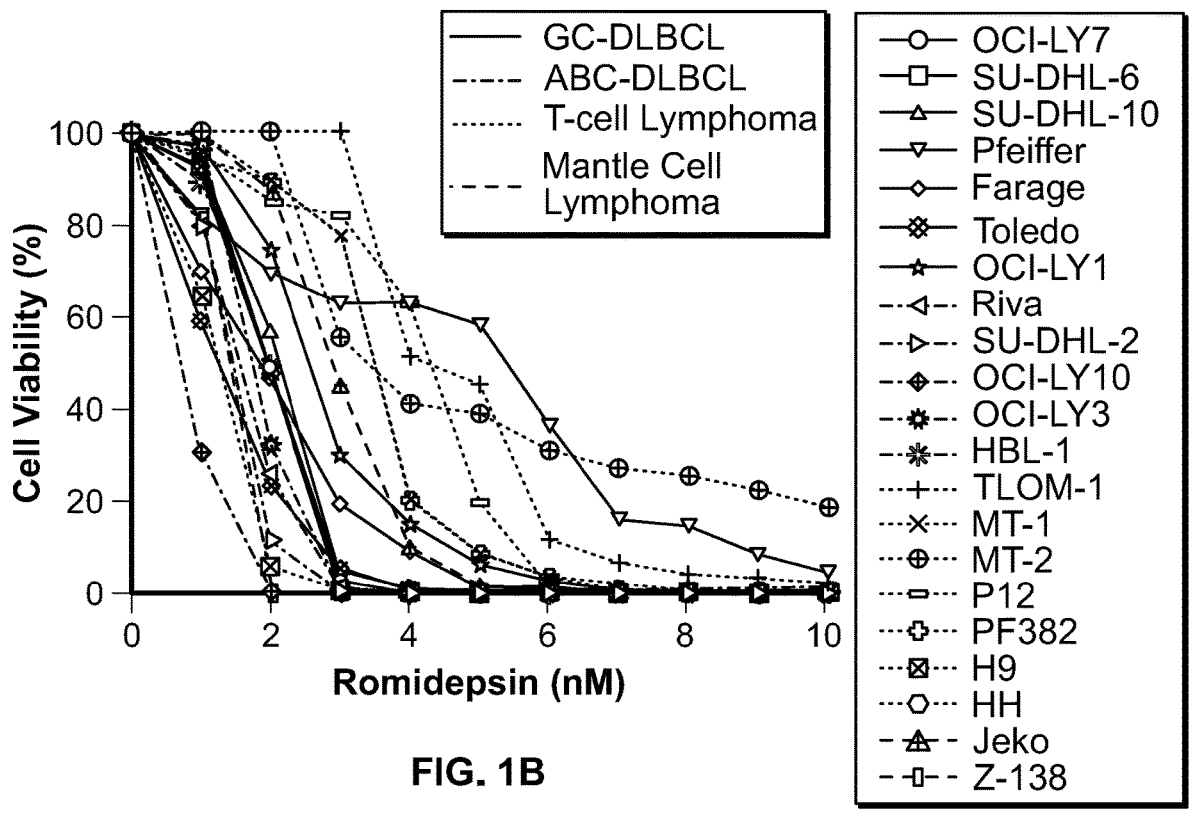

To understand the effects of EZH2 inhibition and HDAC inhibition in cell lines with or without EZH2 dysfunction and HAT mutations, a panel of 21 lymphoma cell lines were exposed to GSK126, an EZH2 inhibitor, and romidepsin, a pan-HDAC inhibitor, as single agents. Both B-cell and TCL were selected in order to establish a range of drug sensitivity and mutational status. EZH2 status and HAT mutational status were confirmed. The concentration:effect relationship of 21 cell lines were established over varying time exposures and increasing concentrations to determine the IC50 to GSK126 and romidepsin (FIGS. 1A-1B).

Table 4 shows IC50 values (144 hours) for respective cell lines after exposure to GSK126. Dysfunction is defined as overexpression of EZH2 and mutated EZH2 combined.

TABLE 4

| Cell Lines | Subtype | EZH2 Status | IC50 GSK126 (µM) |
|---|---|---|---|
| Pfeiffer | GC-DLBCL | A677G | 0.1 |
| SU-DHL-10 | GC-DLBCL | Y641F; Y646S | 0.7 |
| TLOM-1 | ATLL | Overexpression | 1.5 |
| SU-DHL-6 | GC-DLBCL | Y602N; Y646N | 3.1 |
| OCI-LY1 | GC-DLBCL | Y602N; Y646N | 3.7 |
| HBL-1 | ABC-DLBCL | Wildtype | 4.2 |
| OCI-LY7 | GC-DLBCL | Wildtype | 4.3 |
| MT-1 | ATLL | Overexpression | 4.4 |

TABLE 4-continued

| | | | |
|---|---|---|---|
| HH | CTCL | Wildtype | 4.4 |
| SU-DHL-2 | ABC-DLBCL | Wildtype | 4.4 |
| PF-382 | T-ALL | Wildtype | 5.6 |
| Toledo | GC-DLBCL | Wildtype | 6 |
| P12 | T-ALL | Wildtype | 6 |
| H9 | CTCL | Wildtype | 6.1 |
| OCI-LY10 | AB C-DLBCL | Wildtype | 6.4 |
| Z-138 | Mantle Cell | Overexpression | 7.1 |
| OCI-LY3 | ABC-DLBCL | Wildtype | 7.2 |
| Riva | ABC-DLBCL | Wildtype | 7.5 |
| MT-2 | ATLL | Overexpression | 9 |
| Jeko-1 | Mantle Cell | Overexpression | 10 |
| Farage | GC-DLBCL | Wildtype | 10 |

| | p-value |
|---|---|
| Dysfunction vs. WT | 0.15 |
| Mutated vs. WT | 0.02 |
| OE vs. WT | 0.52 |

Table 5 shows IC50 values after 72-hour exposure to romidepsin. There is a trend towards the presence of HAT mutation and sensitivity to romidepsin (p=0.05).

TABLE 5

| Cell Lines | Lymphoma | EP300/CREBBP | IC50 Romidespin (nM) |
|---|---|---|---|
| OCI-LY10 | ABC-DLBCL | EP300 non sen mut/CREBBP non ses mut | 1.0 |
| HBL-1 | ABC-DLBCL | Wildtype | 1.0 |
| Toledo | GC-DLBCL | EP300 mis mut/CREBBP del | 1.0 |
| Z-138 | Mantle Cell | Wildtype | 1.1 |
| Jeko-1 | Mantle Cell | Wildtype | 1.1 |
| HH | CTCL | Wildtype | 1.1 |
| SU-DHL-2 | ABC-DLBCL | Wildtype | 1.3 |
| H9 | CTCL | Wildtype | 1.3 |
| Riva | ABC-DLBCL | Wildtype | 1.5 |
| OCI-LY7 | GC-DLBCL | Wildtype | 1.5 |
| Farage | GC-DLBCL | EP300 fs/CREBBP mis mut | 1.7 |
| OCI-LY3 | ABC-DLBCL | Wildtype | 1.7 |
| SU-DHL-6 | GC-DLBCL | EP300 mis mut/CREBBP trunc mut | 2.0 |
| SU-DHL-10 | GC-DLBCL | EP300 mis mut/CREBBP trunc mut | 2.1 |
| OCI-LY1 | GC-DLBCL | CREBBP del | 2.5 |
| MT-2 | ATLL | Wildtype | 2.7 |
| MT-1 | ATLL | Wildtype | 2.8 |
| PF-382 | T-ALL | CREBBP mis mut | 3.5 |
| TLOM-1 | ATLL | Wildtype | 4.3 |
| P12 | T-ALL | Wildtype | 4.3 |
| Pfeiffer | GC-DLBCL | CREBBP mis mut | 6.0 |

| | P-value |
|---|---|
| Mutated vs. WT | 0.05 |

Lymphoma cell lines with an activating mutation in EZH2 were more sensitive to GSK126 as compared to wildtype EZH2 (p=0.02) as rank ordered by the IC50 at 144 hours (FIGS. 1A, 1C). In regards to cell lines with EZH2 overexpression, there was no clear association with increased sensitivity to GSK126 as compared to wildtype (p=0.52). A trend towards romidepsin sensitivity and the presence of EP300 or CREBBP mutation was observed (p=0.05) (FIGS. 1B, 1D).

Figure 2A:
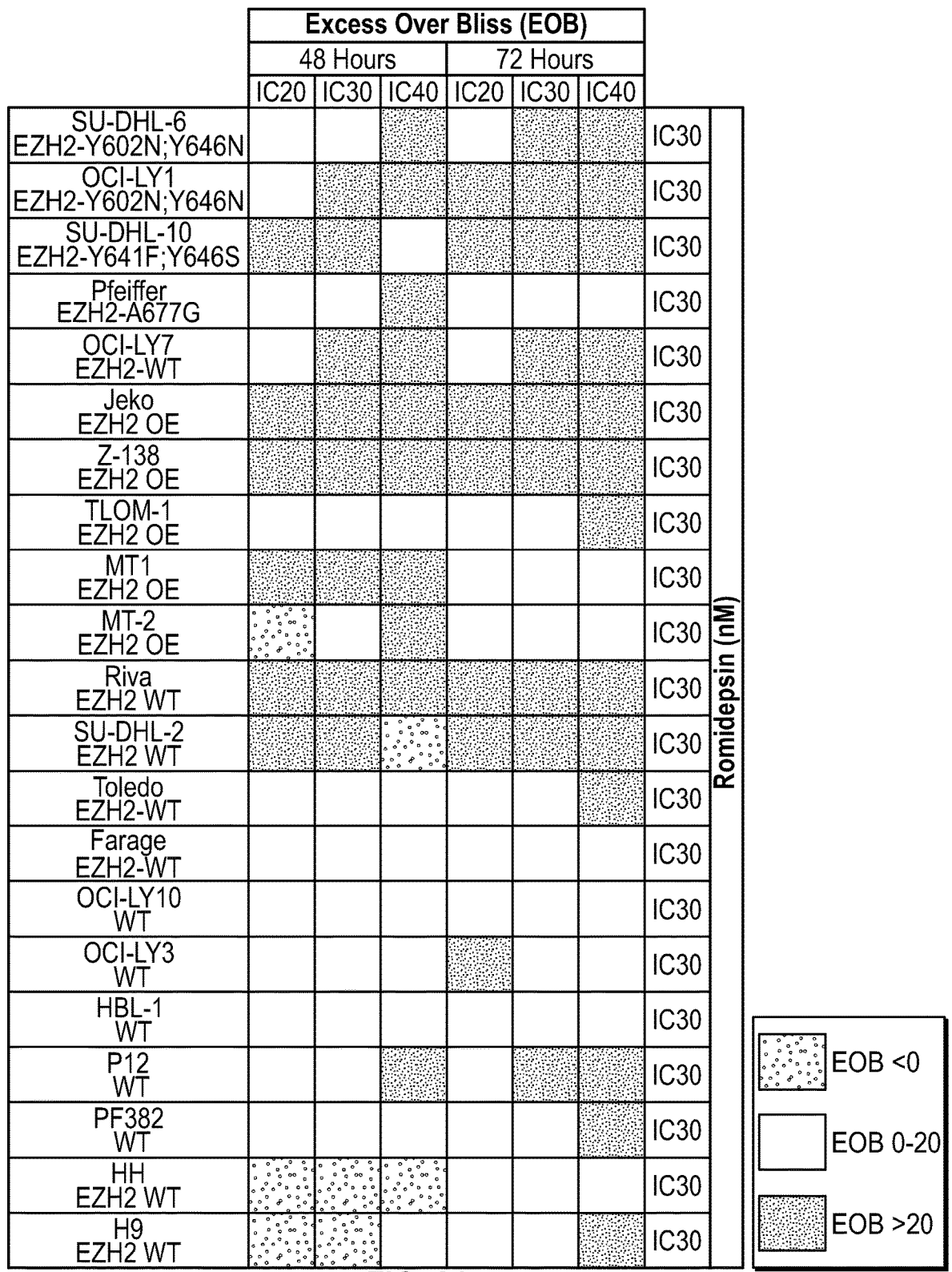
FIGS. 2A-2F. GSK126 and romidepsin are synergistic in EZH2 dysregulated lymphomas. A. 72-hour co-exposure of GSK126 (G) and romidepsin (R) lead to potent synergy in lymphoma cell lines with EZH2 dysregulation as measured by Excess over Bliss (EOB). B-E. G+R induces apoptosis in 4 germinal center DLBCL cell lines (OCI-LY7, SU-DHL-6, SU-DHL-10, and Pfeiffer) at 48 hours as demonstrated by flow cytometry. F. The combination of G+R leads to increase levels of p21, in turn, leading to apoptosis of 4 germinal center derived lymphomas as depicted by cleavage of PARP and increased pro-Caspase-3 levels.
Figure 2B:
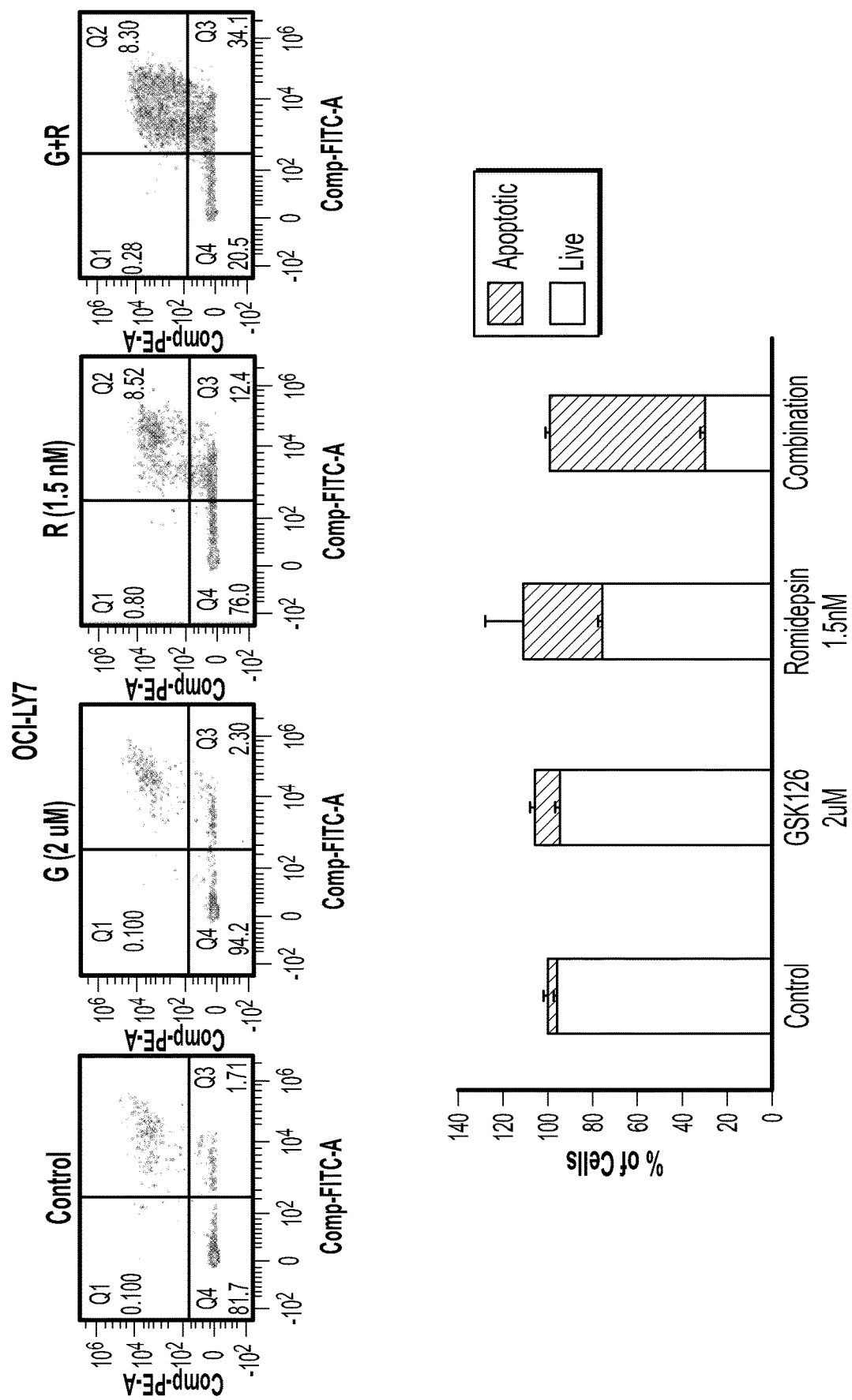
Figure 2C:
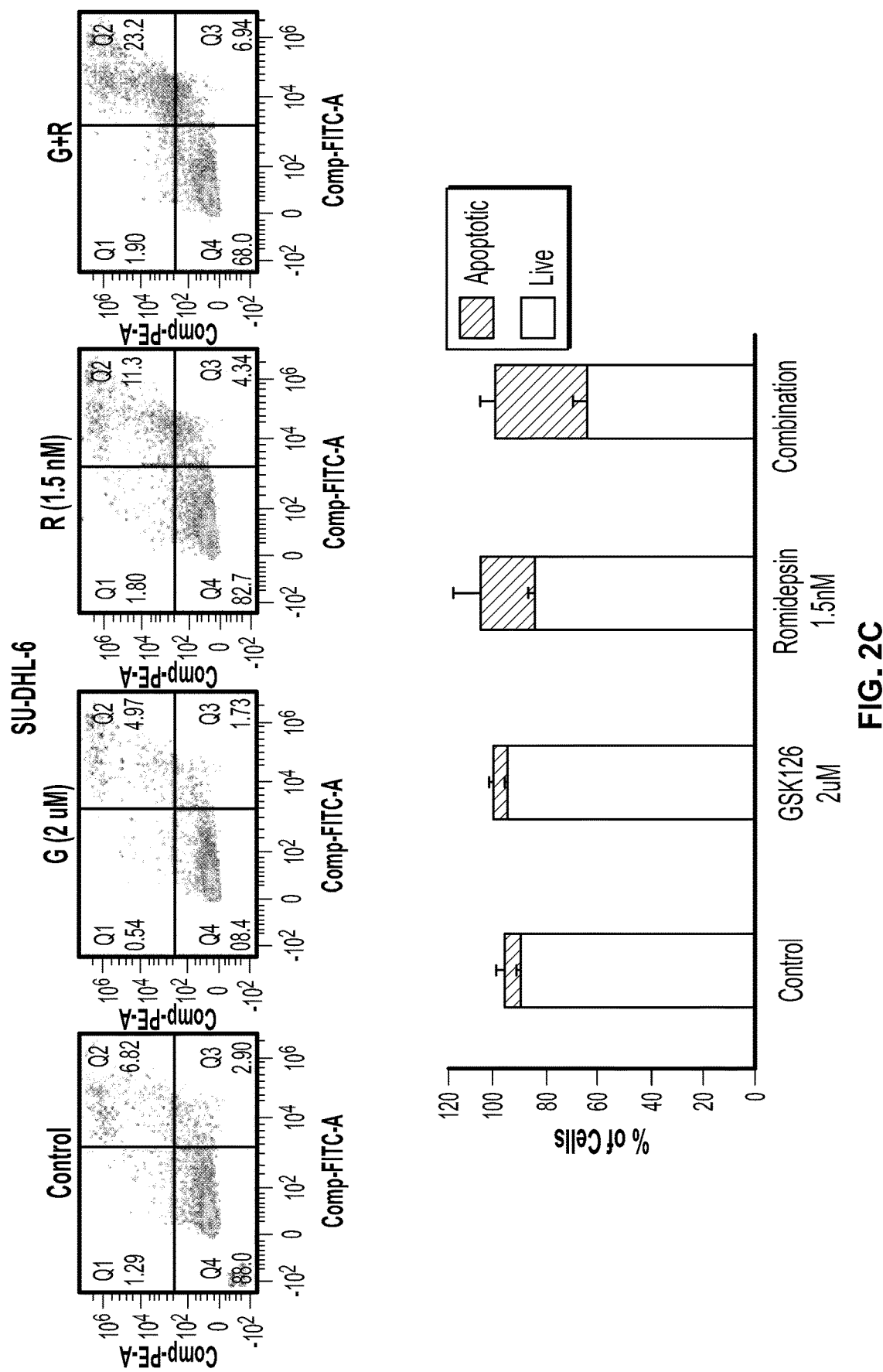
Figure 2D:
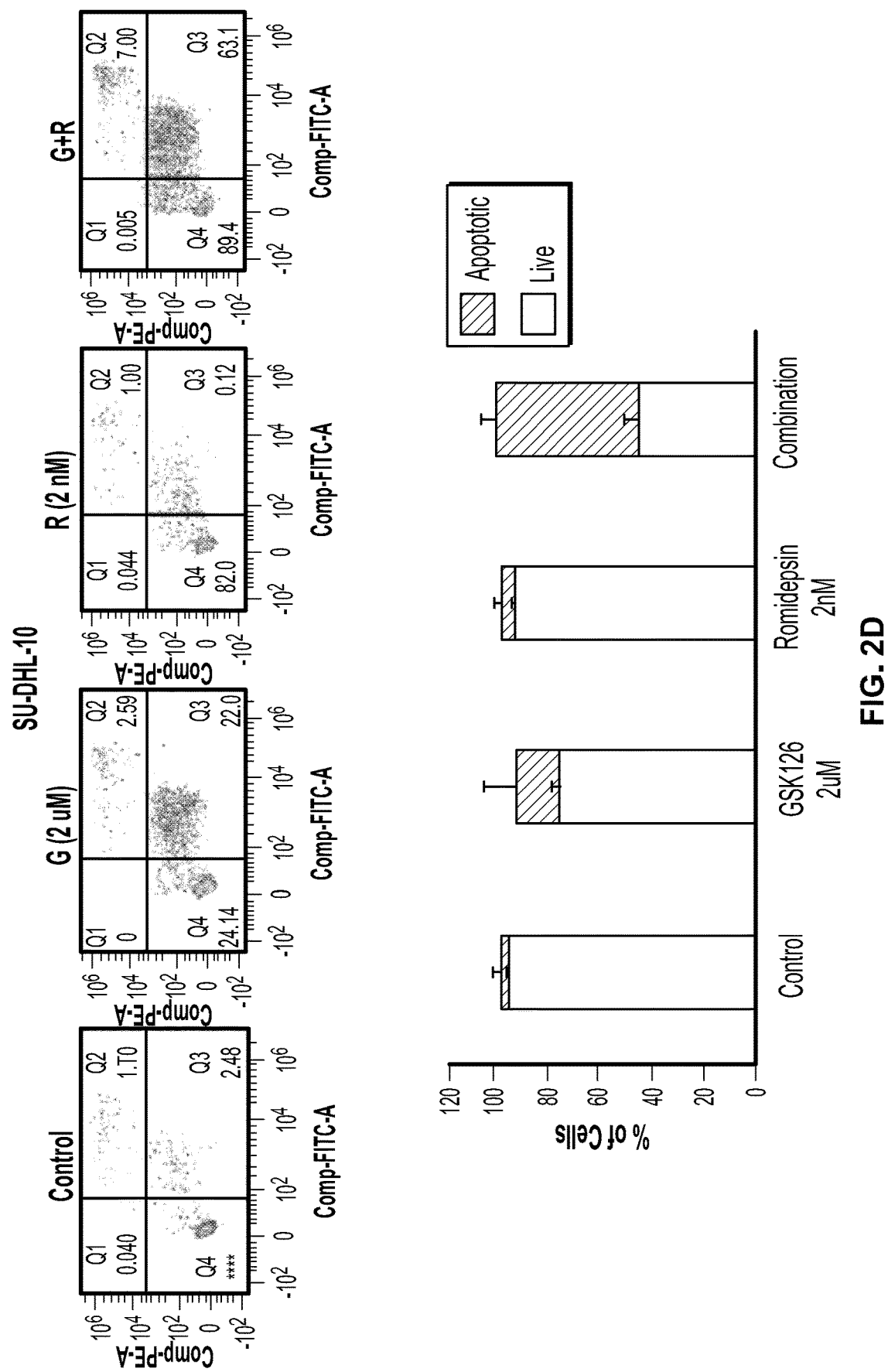
Figure 2E:
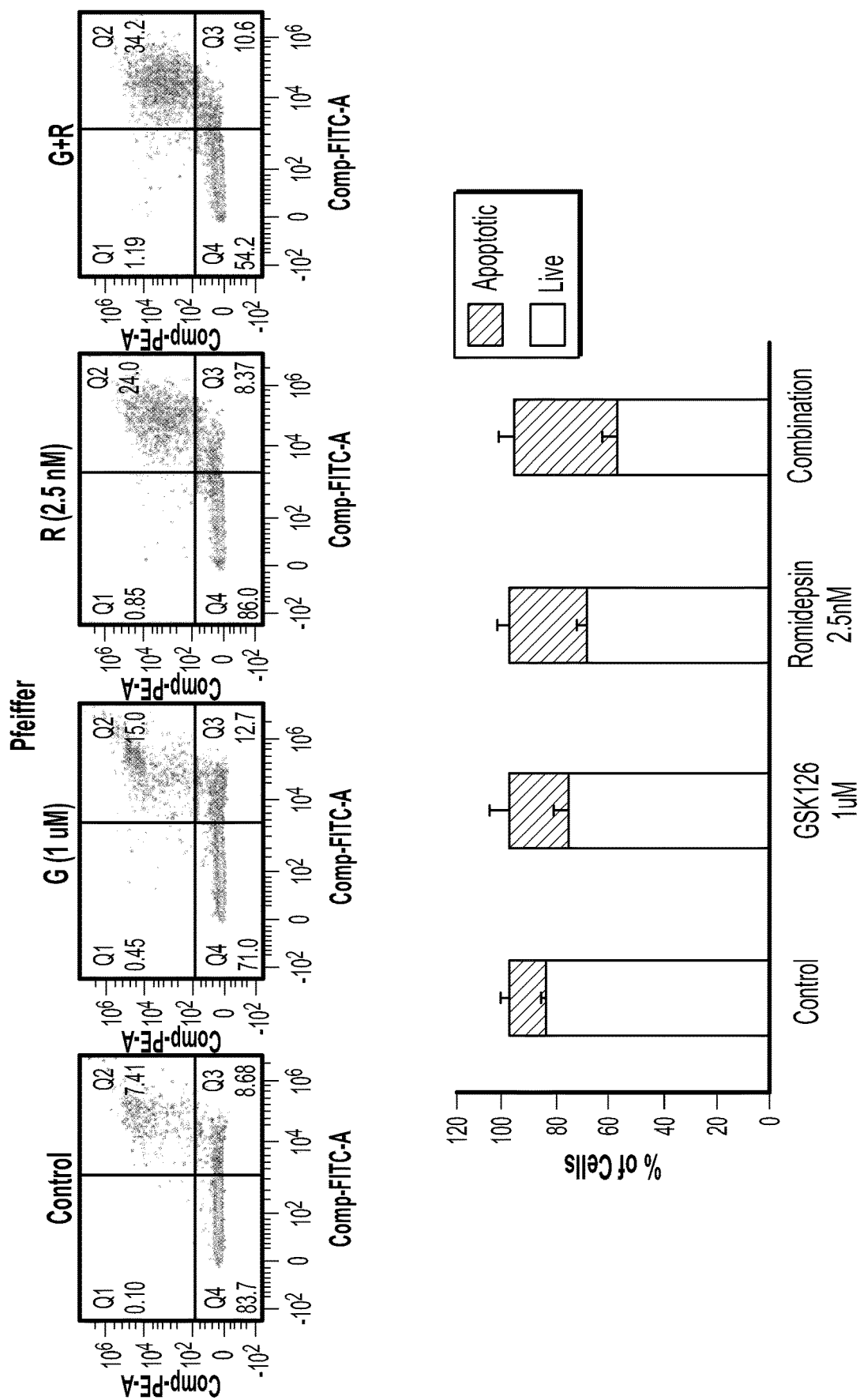
Figure 7A:
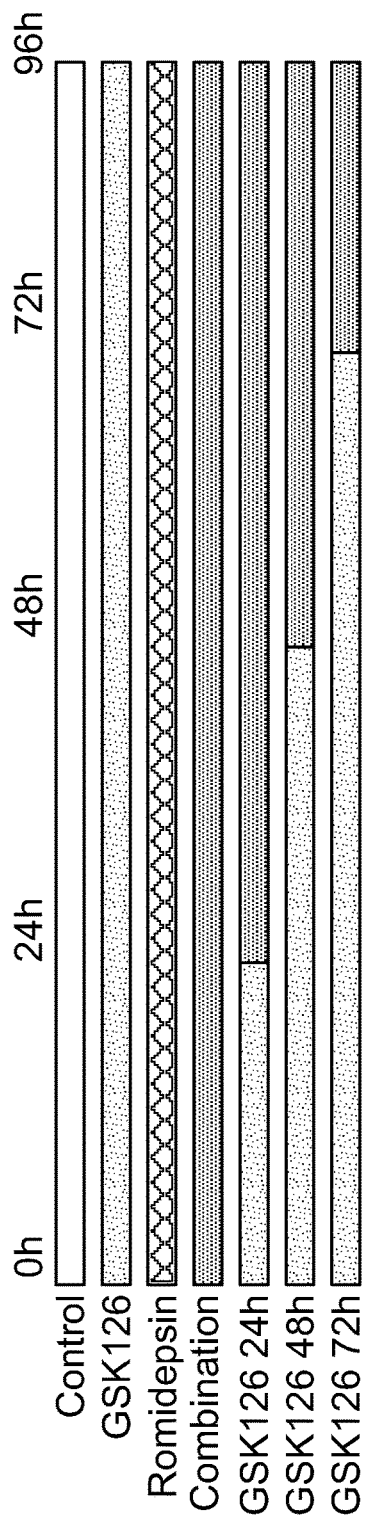
FIGS. 7A-7D show the effect of GSK126 pre-treatment. A. In vitro pre-treatment schema model. B. Pre-treatment with GSK126 (24 h, 48 h, 72 h) followed by romidepsin addition did not impact synergy. C. One-week pre-treatment with GSK126 followed by addition of romidepsin in SU-DHL-10 xenograft model. D. There was no significant difference (p>0.05) in tumor growth between pre-treatment combination and simultaneous combination with GSK126 and romidepsin in a mouse model.
Figure 7B:
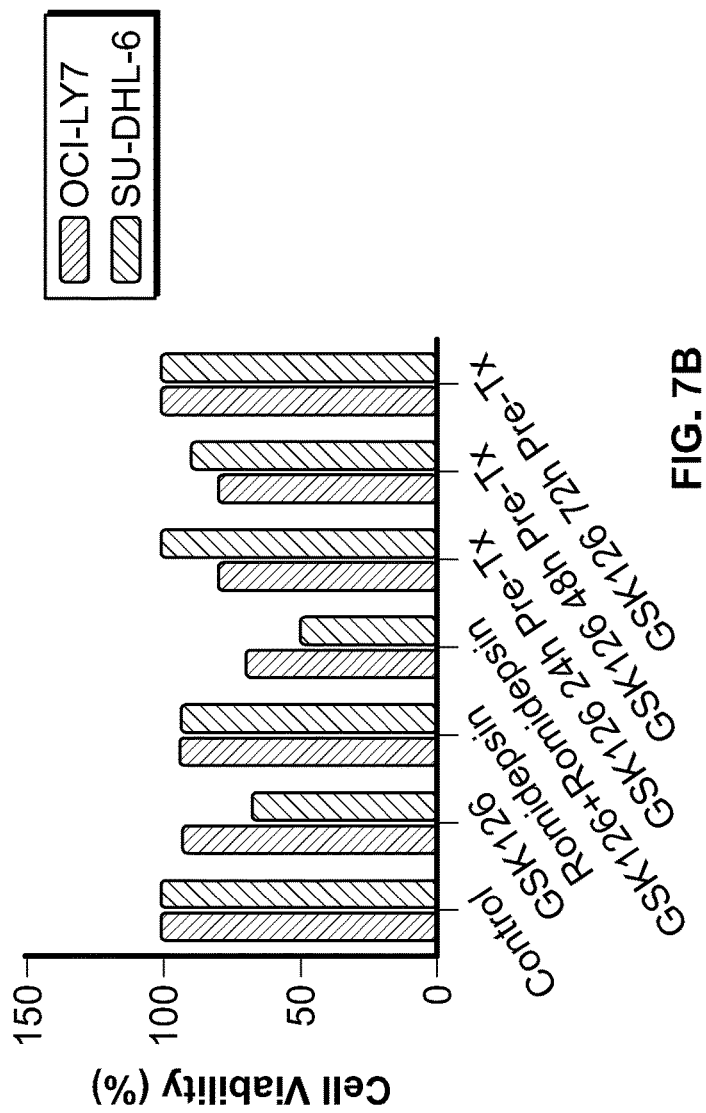
Figure 7C:
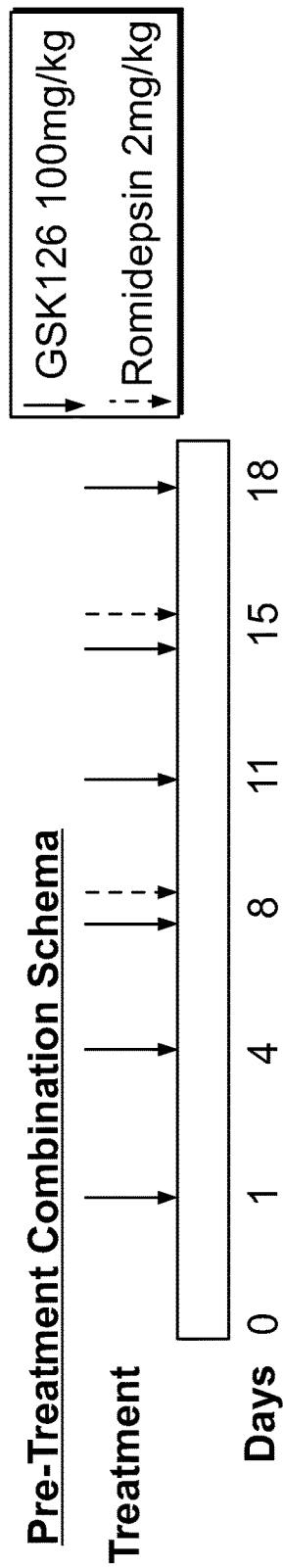
Figure 7D:
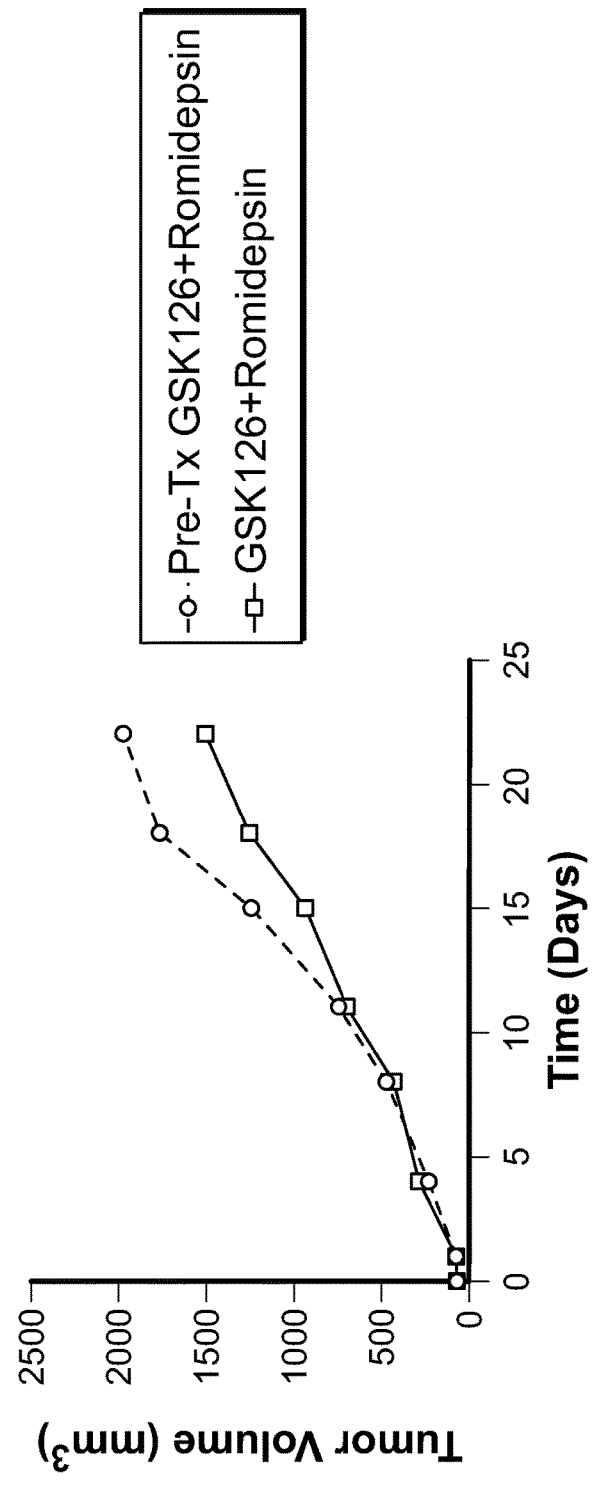
Figure 8D:
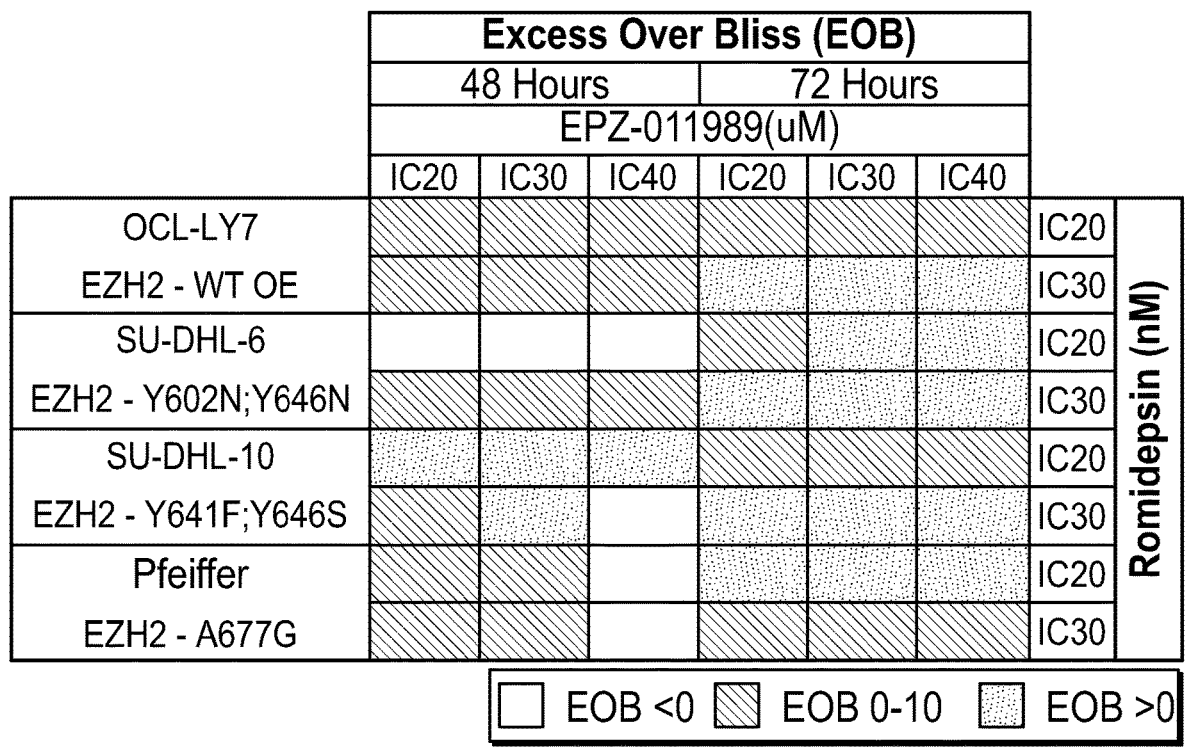
Figure 8E:
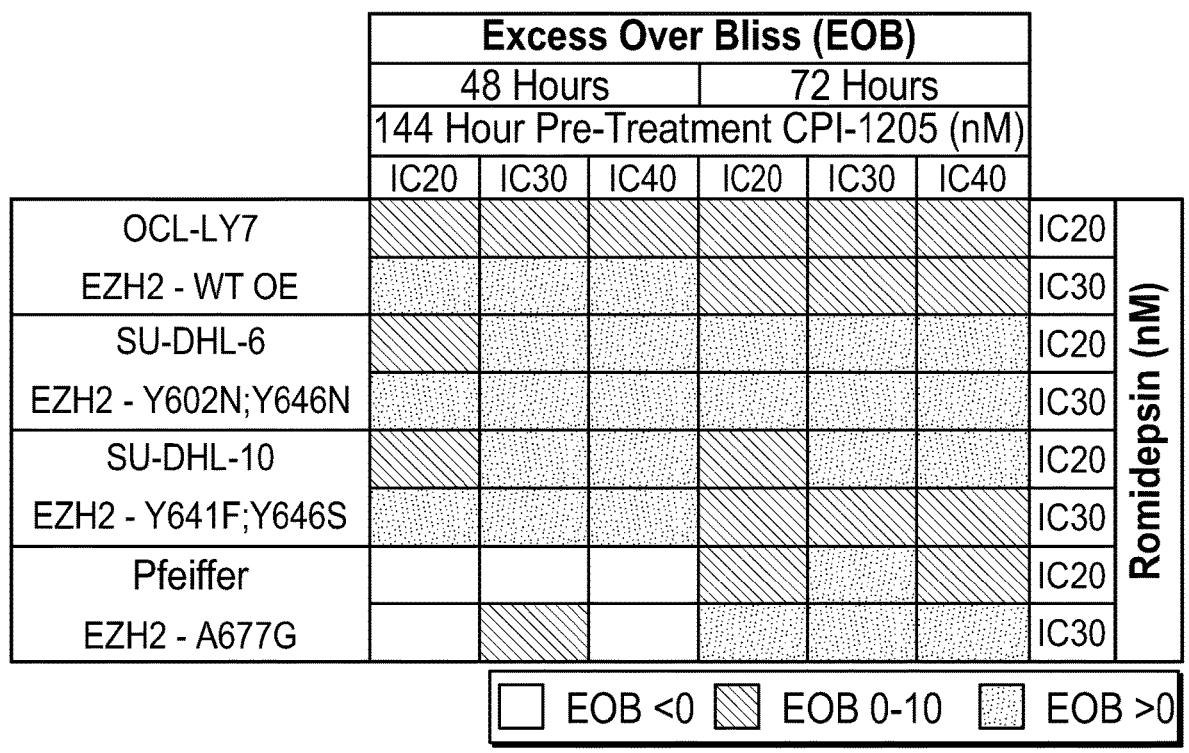

To investigate the dual effects of EZH2 inhibition and HDAC inhibition, lymphoma cell lines were simultaneously exposed to GSK126 and romidepsin over 48 and 72 hours. Cells were characterized by EZH2 dysregulation: (1) activating mutation, (2) wild-type. Co-exposure to GSK126 (an EZH2 inhibitor) and romidepsin demonstrated potent synergy with the highest EOB value reaching 61.7 (FIG. 2A). Cell lines harboring EZH2 mutations demonstrated the highest level of synergy. Drug schedule with pre-treatment of GSK126 was evaluated but did not impact synergy (FIG. 8A). Combination of romidepsin with other EZH2 inhibitors including EPZ-011989 and CPI-1205 also demonstrated synergy showing that the combination of EZH2 inhibition and romidepsin is a class effect of EZH2 (FIGS. 7A-7D).

FIG. 2A is a heat map showing synergy of the combination of GSK126, an EZH2 inhibitor, and romidepsin in GC-DLBCL, in EZH2 wild type-over expressed and mutated EZH2. Synergy was observed in cell lines of other lymphoma subtypes also known to have overexpression of EZH2. The heat map represents synergy coefficients where EOB≥20 (and/or EOB 0-20) indicates synergy. GSK: 0.5-6.5 µM, romidespsin: 1.0-4.0 nM, EOB range: −22.5 to 61.7. Drug schedule did not impact synergy. Data demonstrated synergy of the combination of GSK126, an EZH2 inhibitor, and romidepsin in GC-DLBCL, both in EZH2 wild type-over expressed or mutated EZH2 (FIG. 2A). Synergy was observed in cell lines of other lymphoma subtypes also known to have overexpression of EZH2. Evaluation of drug schedule, with pre-exposure to EZH2 inhibitors followed by HDAC inhibitors, did not enhance synergy.

The combination of EZH2 and HDAC inhibitors (GSK126 and romidepsin) led to increased histone acetylation (H3K27-ac) and decreased trimethylation of histone (H3K27-me3) to a greater degree than control, GSK126 alone, and romidepsin alone. See Table 2.

TABLE 2

| Cohort | n | Treatment Days |
| --- | --- | --- |
| Control | 10 | D1, 4, 8, 11, 15, 18, 22, 25 |
| GSK126 | 9 | D1, 4, 8, 11, 15, 18, 22, 25 |
| Romidepsin | 9 | D1, 8, 15 |
| GSK126+ Romidepsin | 10 | GSK126: D1, 4, 8, 11, 15, 18, 22,25 Romidepsin: D1, 8, 15 |

In addition, combination therapy led to decreased expression of PRC2 complex members and increased p21, in turn inducing apoptosis of lymphoma cells, which was confirmed by decrease pro-caspase 3 and increase PARP cleavage. Dissociation of cofactors of the PRC2 complex as well as dissociation of HDAC2 and DNMT3L as assessed by co-immunoprecipitation was observed. A xenograft mouse model of SUD-HL10 (EZH2 mutated) treated with EZH2 inhibitor, romidepsin or the combination revealed that the combination induced delayed tumor growth and increased overall survival (p<0.001). The combination was well tolerated with no toxicities observed. Basal gene expression was performed by RNA seq on 18 cell lines. Synergy was correlated with a discrete gene expression signature. Pathway analysis was performed by gene set enrichment analysis (GSEA) which revealed that cell lines sensitive to combined EZH2 and HDAC inhibition correlated with a "chromatin silencing" gene signature (Table 3).

TABLE 3

Figure 2F:
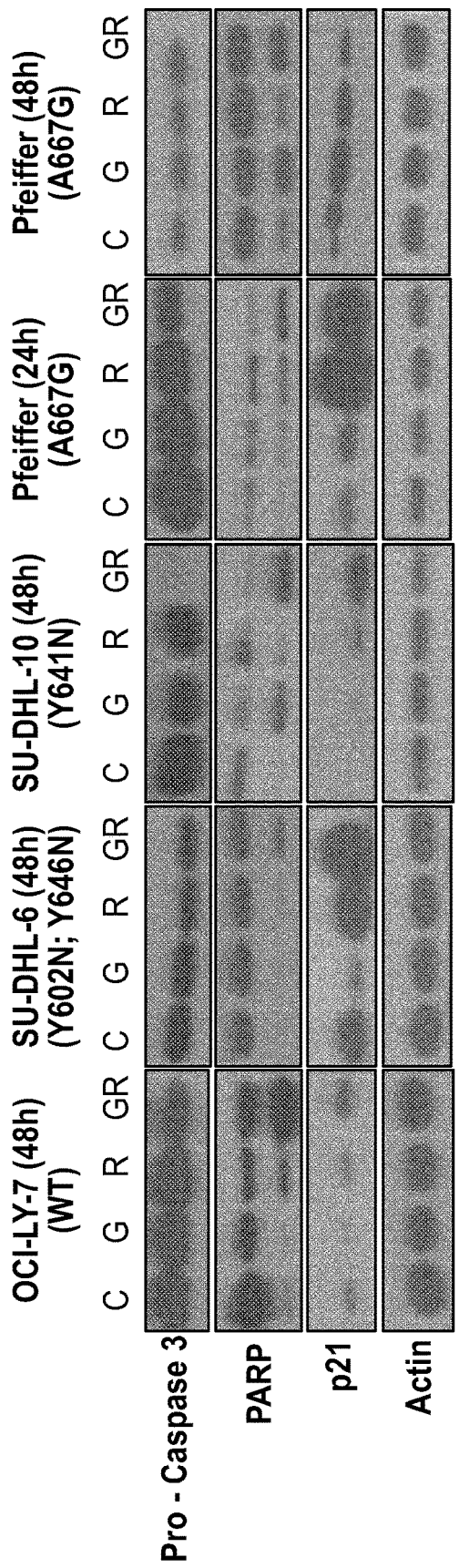

Most common GSEA Biological Pathways Correlated with Synergy ($p < 1^{10}$)
Chromatin Silencing
Negative Regulation of Gene Expression (Epigenetic)
ATP Dependent Chromatin Remodeling
Gene Silencing
Regulation of Gene Expression (Epigenetic)
Protein Acetylation
Positive Regulation of Histone Methylation
Histone H3 Deacetylation To confirm induction of apoptosis, 4 GC-DLBCL cell lines with different EZH2 mutational status were simultaneously treated with GSK126 and romidepsin for 24-48 hours and evaluated by flow cytometry (FIGS. 2B-2E). A time point of 24 hours prior to the maximum EOB value was selected in order to capture the events prior to complete cellular demise (24 hours for Pfeiffer; 48 hours for OCI-LY7, SU-DHL-10, SU-DHL-6). Increased apoptosis was observed with the combination as compared to single agent exposure. Apoptosis was also confirmed by decreased pro-caspase 3 and increased PARP cleavage following exposure to the combination as measured by immunoblot (FIG. 2F). In addition, as compared to single agent treatment, the level of p21 is significantly increased after exposure to GSK126 and romidepsin (FIG. 2F).

Figure 3A:
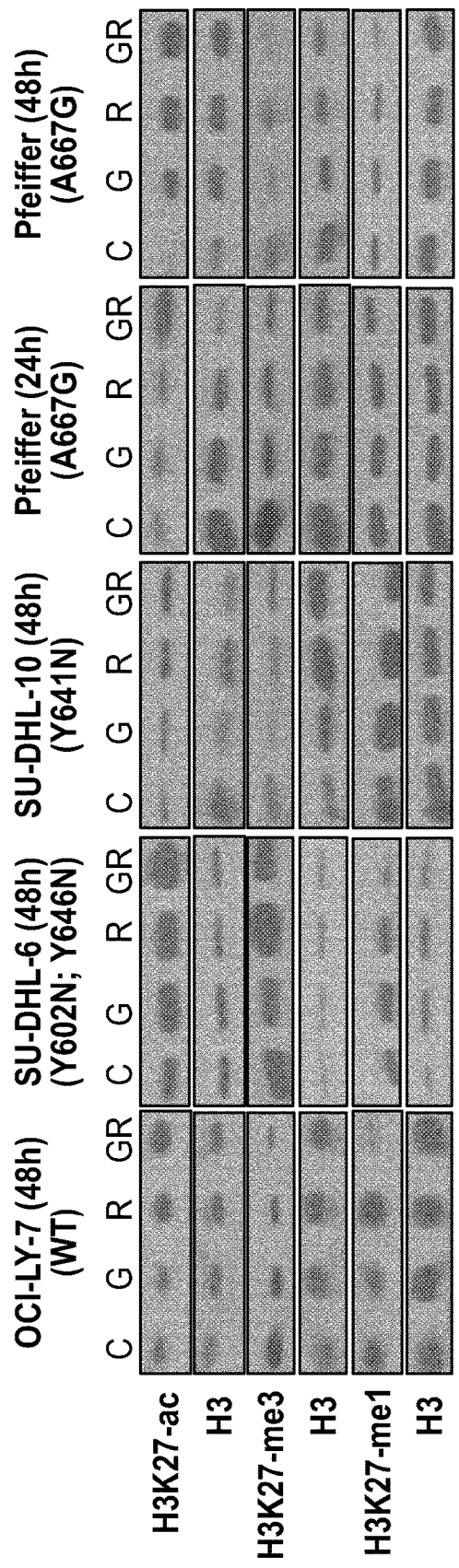
Figure 3B:
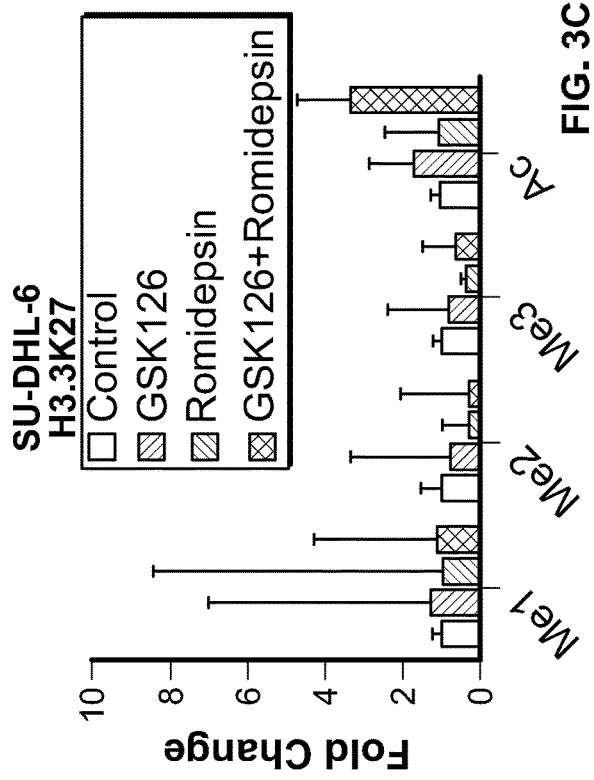
Figure 3C:
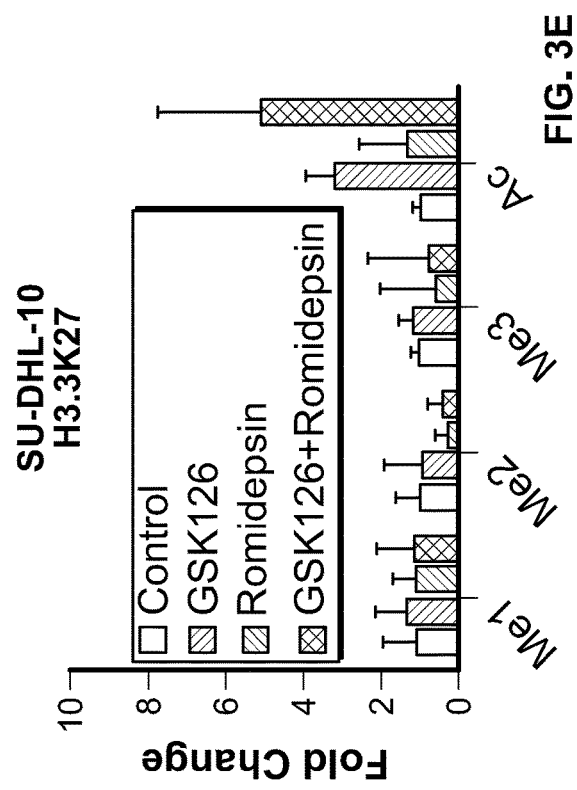
Figure 3D:
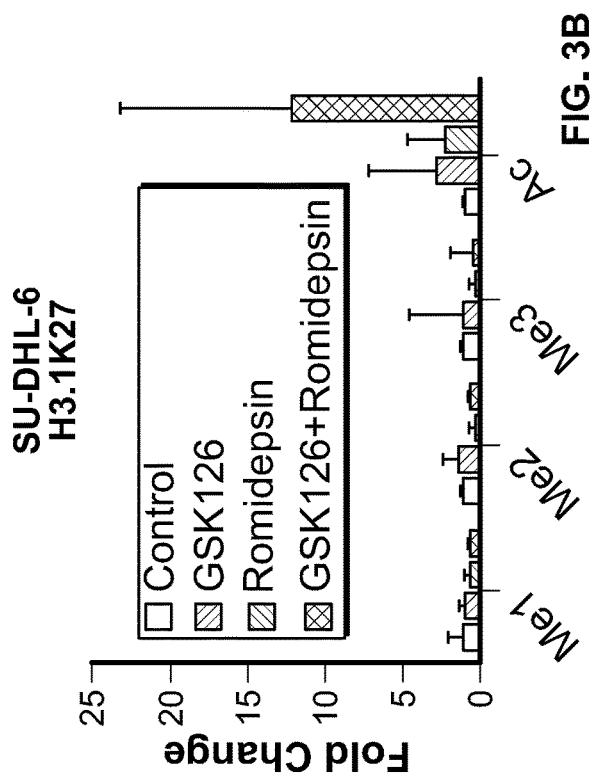
Figure 3E:
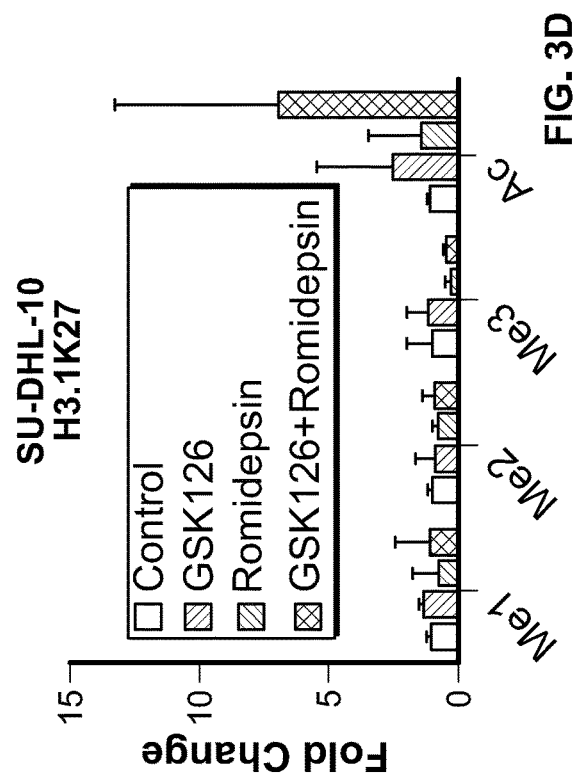

Co-Exposure to GSK126 and Romidepsin Leads to Enhance Acetylation and Hypomethylation of H3K27 as Well as Dissociation of the PRC2 Complex To understand the effects of dual epigenetic targeting on both acetylation and methylation of histone, 4 GC-DLBCL cell lines were exposed to control, GSK126, romidepsin or the combination. Treatment with GSK126 and romidepsin led to increased acetylation and decreased tri-methylation of H3K27 as compared to single agents as detected by histone extraction and immunoblot (FIG. 3A). These findings were validated by mass spectrometry (FIGS. 3B-3E).

Figure 3F:
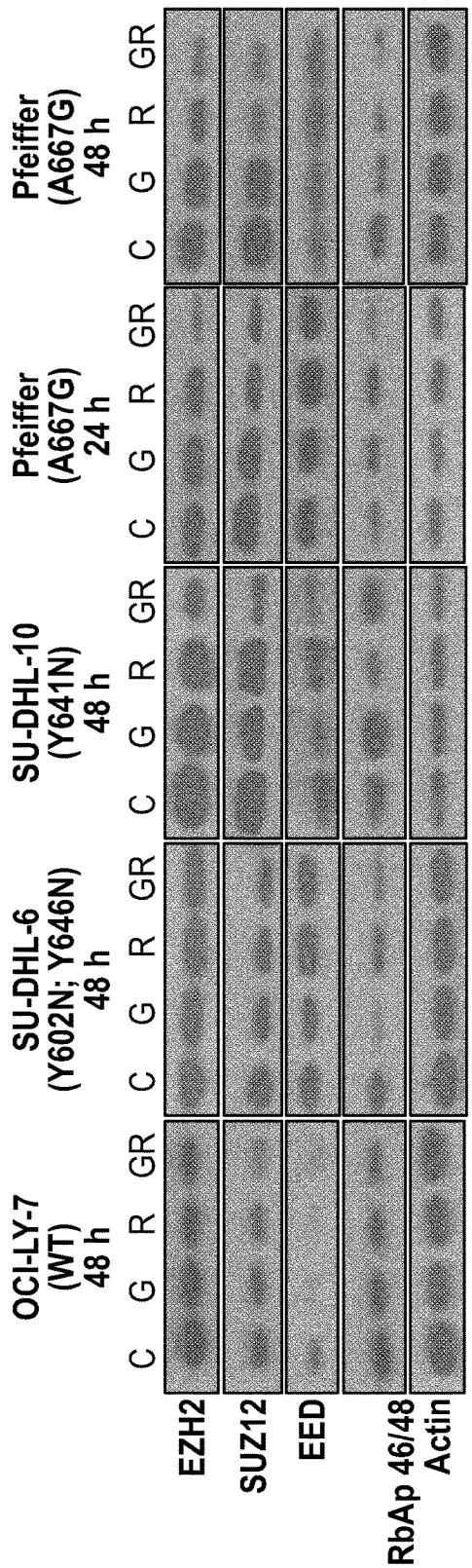
Figure 3G:
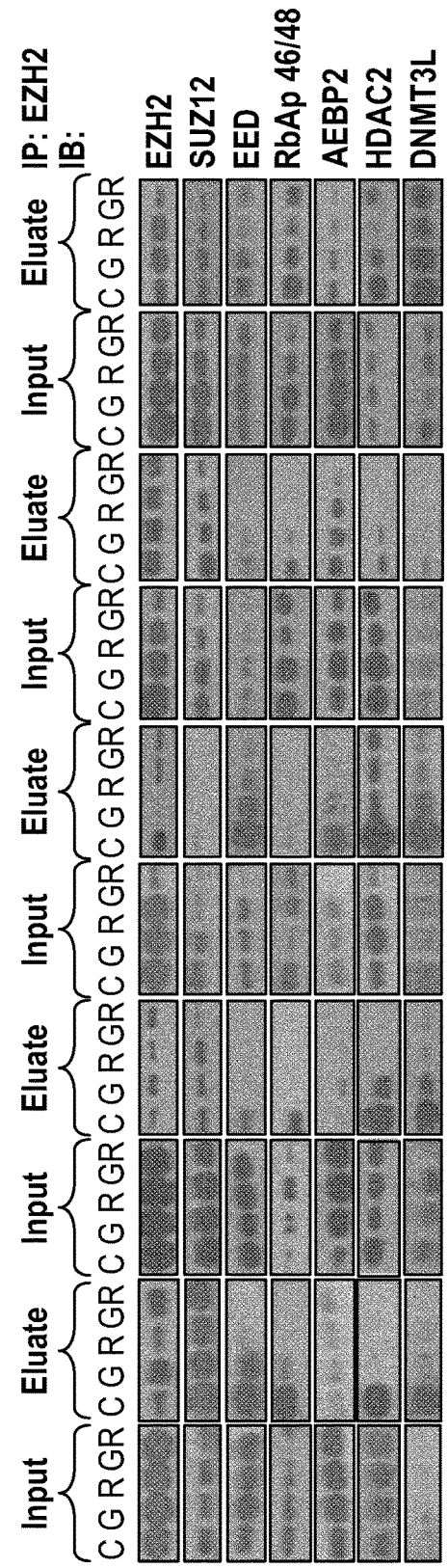

Protein levels of EZH2 and other members of PRC2 complex (SUZ12, EED, RbAp 46/48) were significantly decreased after dual treatment with GSK126 and romidepsin compared to single agent exposure (FIG. 3F). Co-immunoprecipitation pull-down with EZH2 demonstrated dissociation of the PRC2 complex after simultaneous exposure to GSK126 and romidepsin. Specifically, exposure to romidepsin alone or in combination with GSK126 led to dissociation of EZH2 from EED, RbAp 46/48 and AEBP2 as compared to control, suggesting that romidepsin directly contributes to the breakdown of the PRC2 complex (FIG. 3G). In addition, HDAC2 and DNMT3L were also found to disassemble from the EZH2-PRC2 complex after combination therapy. Mass spectrometry confirmed disappearance of members of the PRC2 complex from EZH2 (FIGS. 1H-1I). SU-DHL-10 cells were treated with romidepsin and immunoprecipitation using acetyl-lysine antibodies was performed. Based on mass spectrometry analysis, a 2-fold increase estimated by spectral counts of RbAp 46/48 (RBBP4) was observed after exposure to romidepsin as compared to control (FDR<1.0%) (FIG. 3J). Taken together, this suggests that the disruption of the PRC2 complex is secondary to direct acetylation of RbAp 46/48, which is responsible for PRC2 complex recruitment to nucleosomes 24.

HDAC2 Plays a Critical Role in the Synergy Between GSK126 and Romidepsin

Figure 4A:
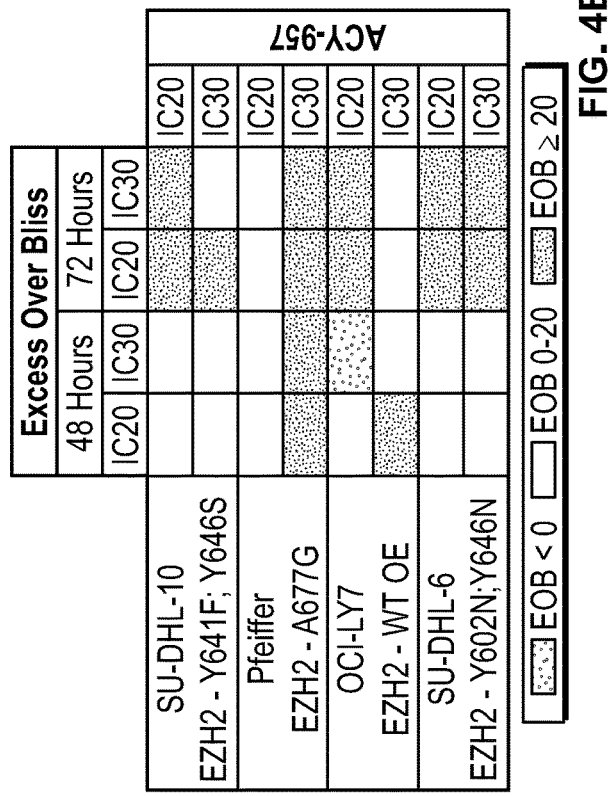
FIGS. 4A-4C. The cooperation of the PRC2 complex and HDAC2 is essential in the synergistic effects of GSK126 and romidepsin. A. Cell viability curves in 4 GC-DLBCL cell lines after exposure to ACY-957 at 72 hours. B. GSK126 and ACY-957 are synergistic as demonstrated by EOB in 4 GC-DLBCL cell lines. C. Acetylation of H3K27 is enhanced by exposure to GSK126 in HDAC2 shRNA HEK 293T cells while methylation levels are attenuated.
Figure 4B:
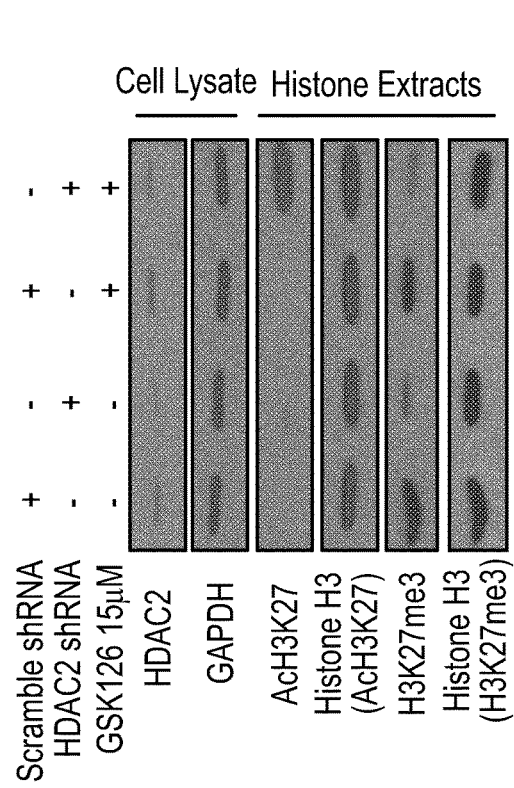
Figure 4C:
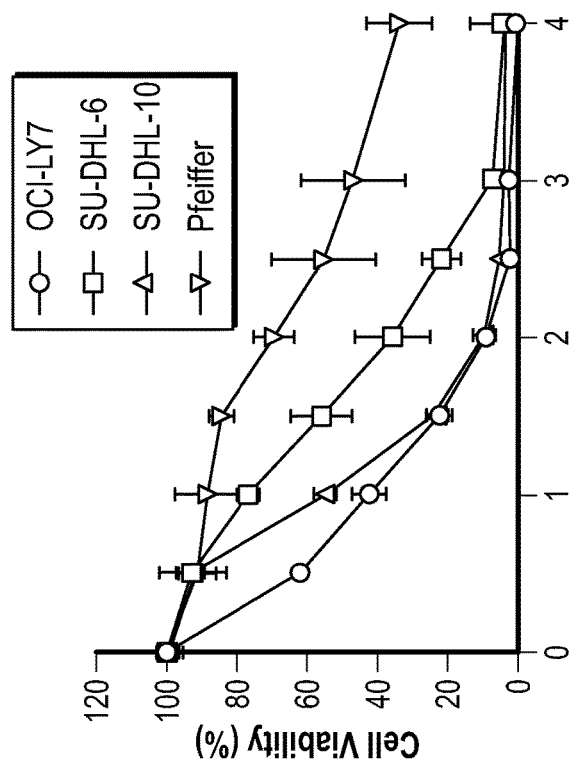

Based on the finding that HDAC2 dissociated from PRC2 complex after dual inhibition of EZH2 and HDACs (FIG. 3D), direct targeting of HDAC2 using a selective HDAC 1/2 inhibitor, ACY957, was combined with GSK126 and was found to be synergistic (FIG. 4B). HDAC2 short hairpin RNA (shRNA) constructs were developed in order to confirm the role of HDAC2 inhibition in the synergy between GSK126 and romidepsin. Increased acetylation of H3K27 was found in HDAC shRNA HEK 293T cells, mimicking the effects of romidepsin, which was further enhanced by treatment with GSK126 (FIG. 4C). Decreased methylation of H3K27 was more pronounced in HDAC2 shRNA cells treated with GSK126, mirroring the effects of GSK126 and romidepsin exposure. Single agent GSK126 exposure in HEK 293T cells did not significantly change the status of acetylation or methylation of H3K27.

Figure 5A:
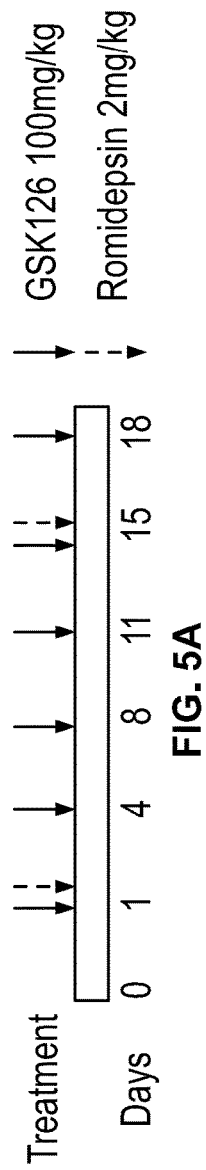
FIGS. 5A-5F. Combination of GSK126 and Romidepsin Improves Overall Survival in a Mouse Xenograft Model. A. Treatment schema. Combination arm received GSK126 on days 1, 4, 8, 11, 15, 18; romidepsin dosed on days 1, 8, 15. B. Combination of GSK126 and romidepsin is tolerable as demonstrated by stability of weight. C. Co-exposure to GSK126 and romidepsin leads to improved tumor control compared to single agent GSK126 or romidepsin. D. Combination of GSK126 and romidepsin leads to improved overall survival compared to single agent GSK126 or romidepsin. E. PK/PD parameters after single intraperitoneal injection of GSK126 and romidepsin. Intratumor GSK126 continues to increase over time and is still present 24 hours. F. Serum romidepsin pharmacokinetic parameters after single injection of GSK and romidepsin over 24 hours.
Figure 5B:
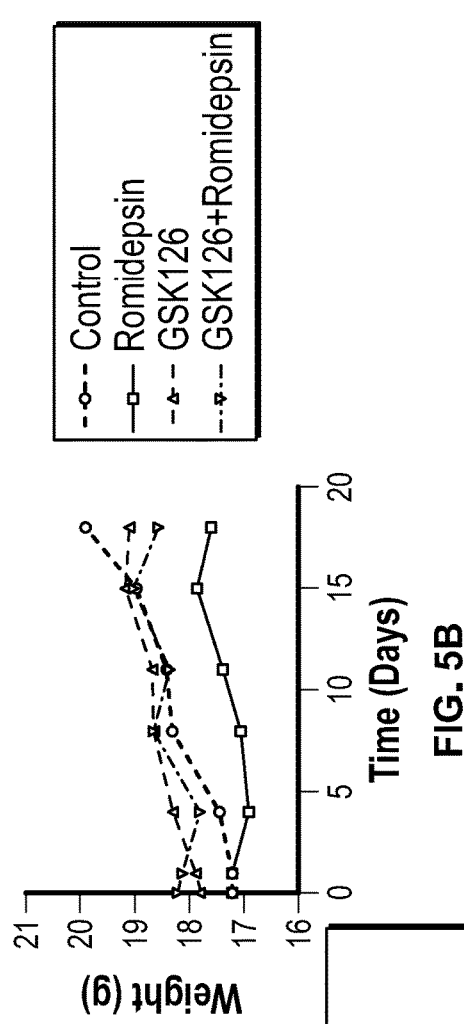
Figure 5D:
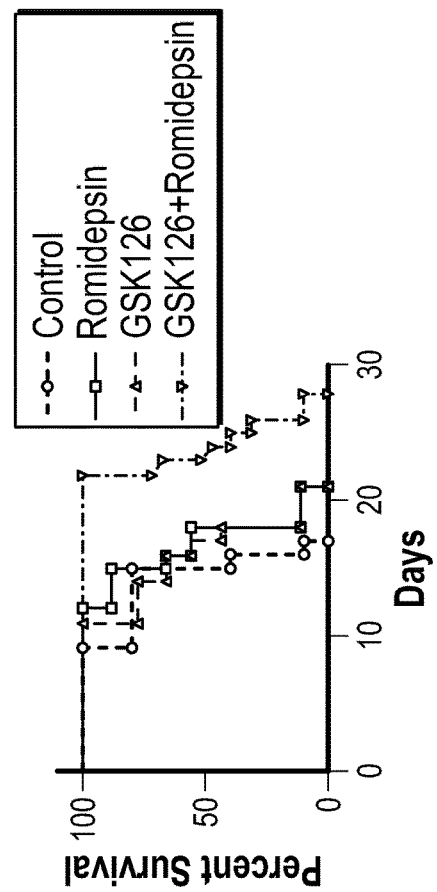
Figure 5C:
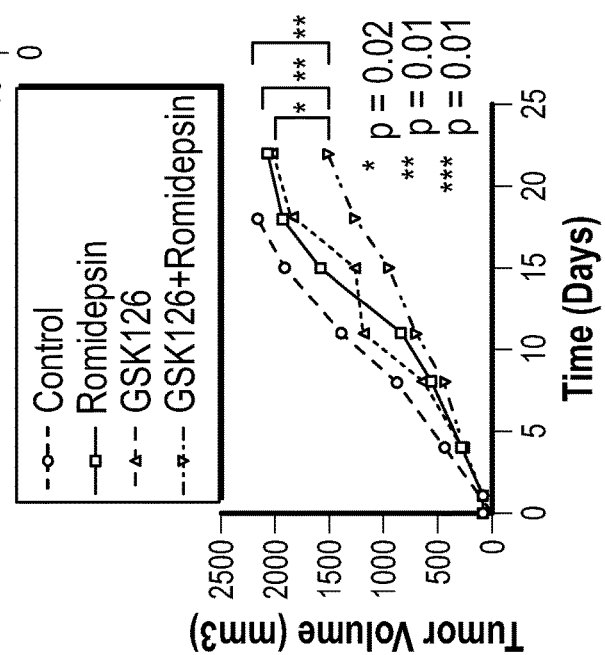

GSK126 and Romidepsin Leads to Improved Overall Survival and Tumor Growth Delay in an In Vivo Mouse Xenograft Model A SU-DHL-10 mouse xenograft model was selected because SU-DHL-10 represents a GC-DLBCL cell line that harbors an EZH2 activating mutation as well as HAT mutations (CREBBP and EP300). Mice were exposed to control, GSK126, romidepsin, or the combination as detailed in FIG. 5A. The combination was well tolerated in mice with no appreciable change in weight (FIG. 5B). Compared to single agent exposure, dual therapy with GSK126 and romidepsin led to significant tumor growth delay (p<0.05), and increase overall survival (p<0.0001) (FIGS. 5C, 5D). Moreover, pre-treatment with GSK126 for 1 week did not improve tumor growth kinetics as compared to simultaneous exposure (FIGS. 7C, 7D).

Figure 5F:
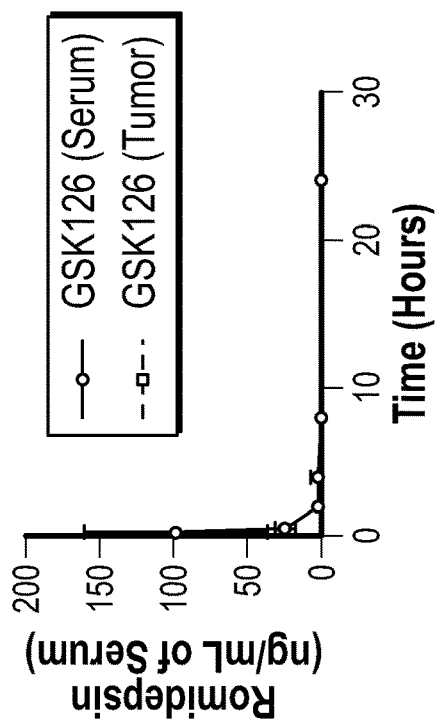
Figure 5E:
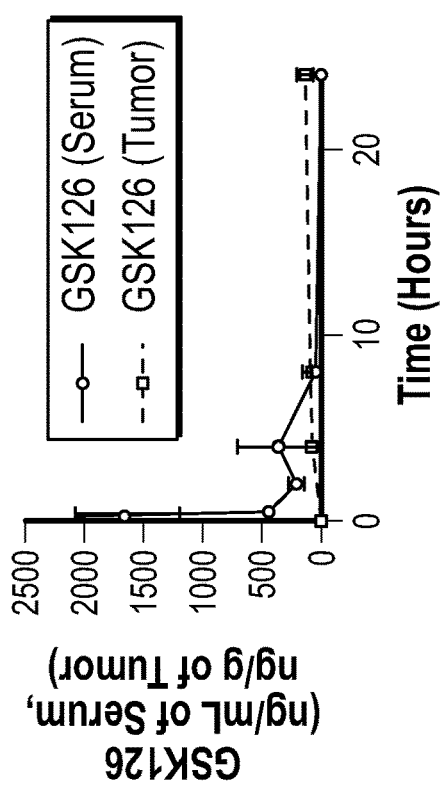

Pharmacokinetic analysis of both serum and tumor samples were performed after a single exposure to GSK126 and romidepsin at various time points. Cmax of GSK126 was 1657.5+/−413.6 ng/mL which translates to 3.15 μM (IC50 of GSK126 in SU-DHL-10 is 0.7 μM), while romidepsin was 25.07+/−7.10 ng/mL or 46.4 nM (IC50 of romidepsin in SU-DHL-10 is 2.59 nM) (FIGS. 5E, 5F). The serum AUC0-last of GSK126 and romidepsin were 2828.57 (h*ng/mL), and 5.51 (h*ng/mL), respectively. The intratumor concentration of GSK126 increased over time, while the romidepsin concentration was below the level of detection.

Figure 6A:
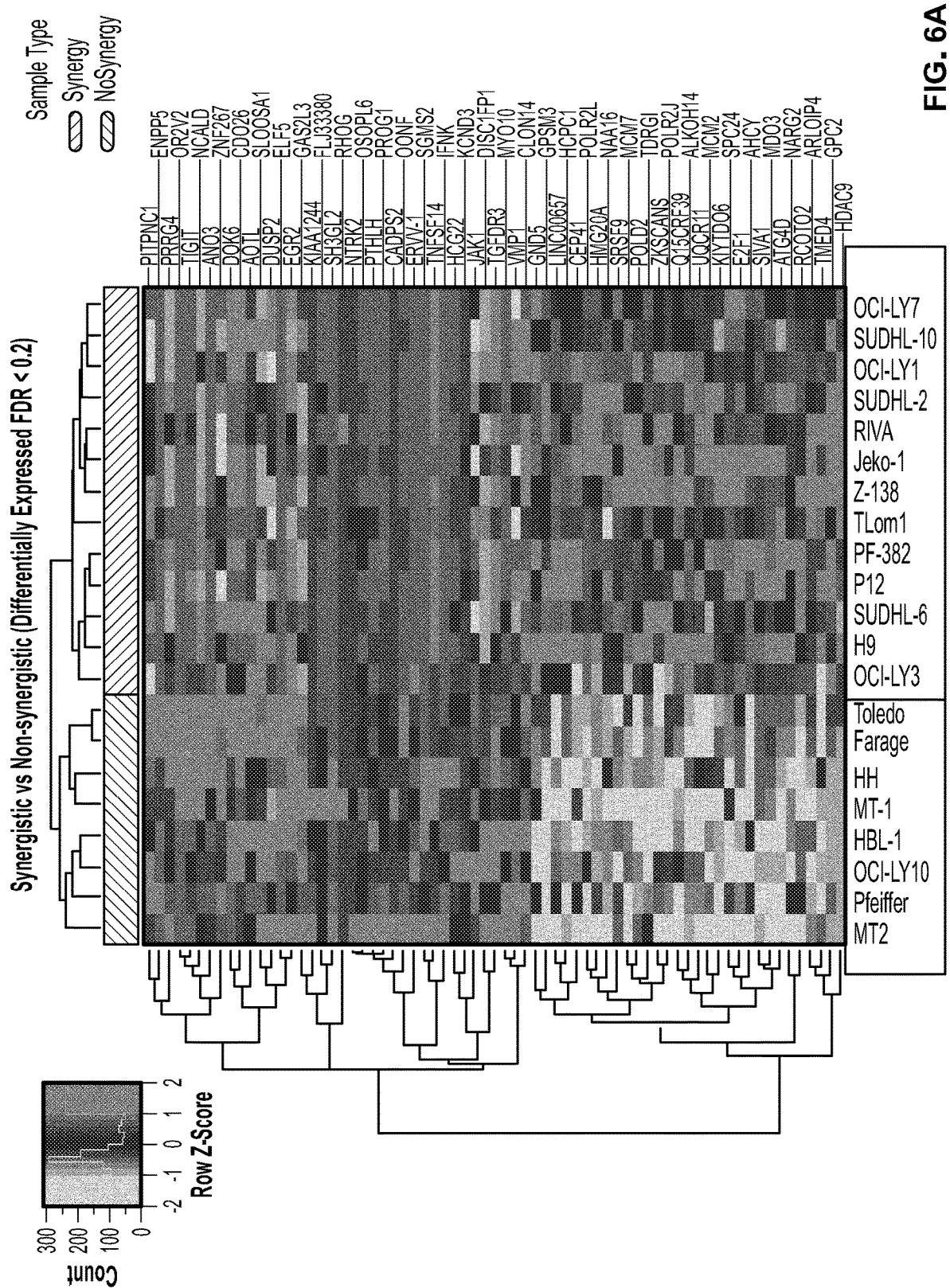
Figure 6B:
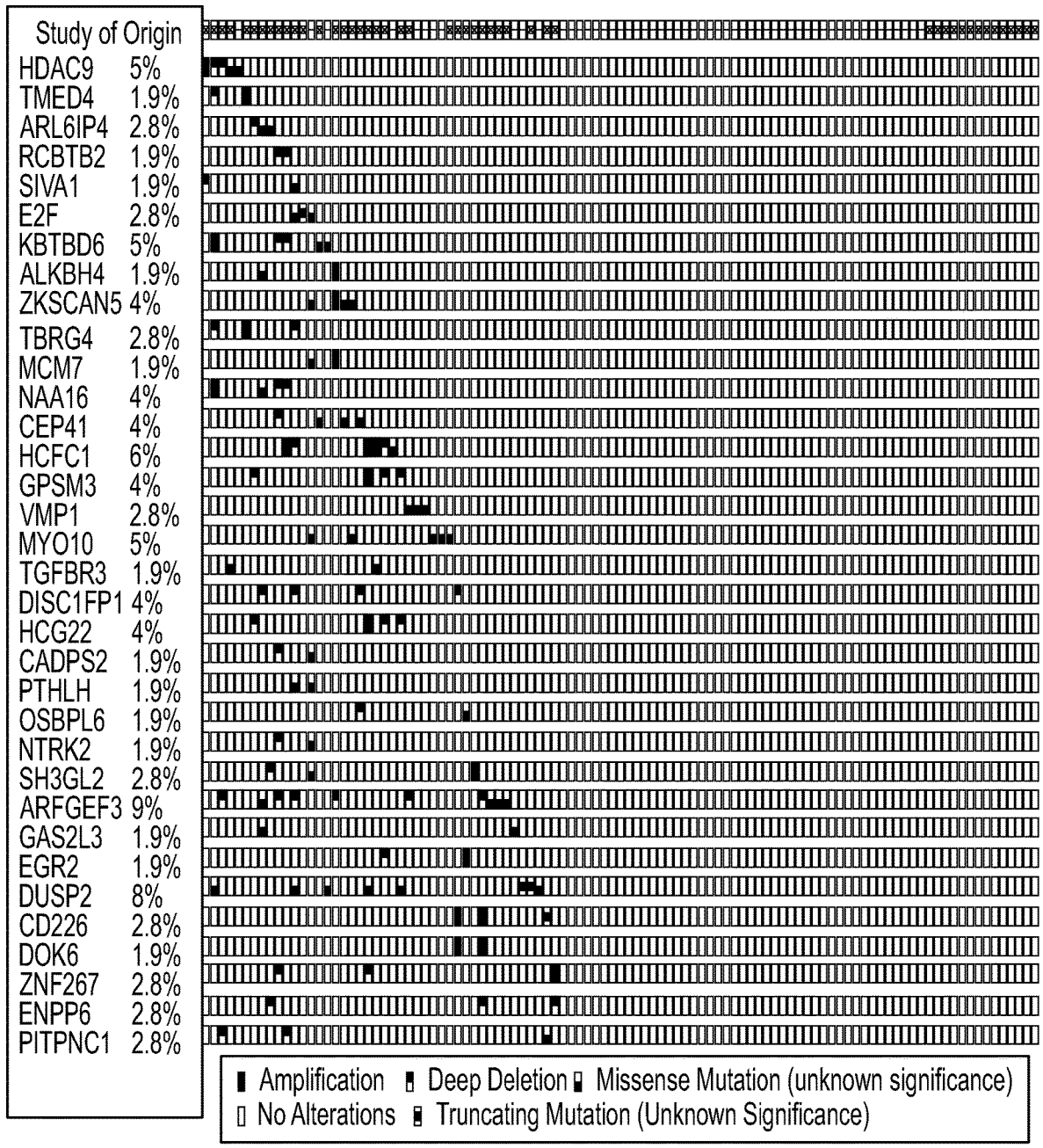

Synergistic Cell Lines Share a Common Basal Gene Expression and Protein Activity Profile Differential gene expression profiling was performed on pre-treatment lymphoma cell lines to determine their basal expression pattern and correlated to synergy (N=21). Cell lines with EOB>20 after treatment with GSK126 and romidepsin were defined as synergistic. There was a total of 69 genes identified (FDR<0.2) that were differentially expressed in the synergistic cell lines compared to non-synergistic cell lines, suggesting that a common basal gene expression profile is shared amongst the synergistic cell lines (FIG. 6A). Pathway analysis determined by gene set enrichment analysis (GSEA) revealed synergistic cell lines are characterized by upregulation in chromatin remodeling genes and transcriptional regulators such as HDAC9 and HCFC1 as well as pathways implicated in epigenetic regulation (FIGS. 6A, 6C). Moreover, of the 69 genes that were found to be differentially expressed in synergistic cell lines compared to non-synergistic cell lines, 34 genes have been identified to be altered in more than 1.0% of primary patient DLBCL samples as confirmed by TCGA database and cBioPortal (FIG. 6B)[26].

metaVIPER was used to identify proteins whose activity predicts, and potentially mediates, sensitivity to dual EZH2-HDAC inhibition in lymphoma cell lines. First, a differential protein activity signature was computed between cell lines that demonstrate synergy by EOB and those that did not, and subsequently performed pathway analysis on this signature. Synergistic cell lines were markedly enriched in pathways involving cell cycle control, DNA replication, and chromatin remodeling (FIG. 6D). This latter finding is similar to what was observed using GSEA at the RNA expression level. Downregulated pathways include inflammatory pathways as well as differentiation/developmental genes (FIG. 6E).

Figure 6F:
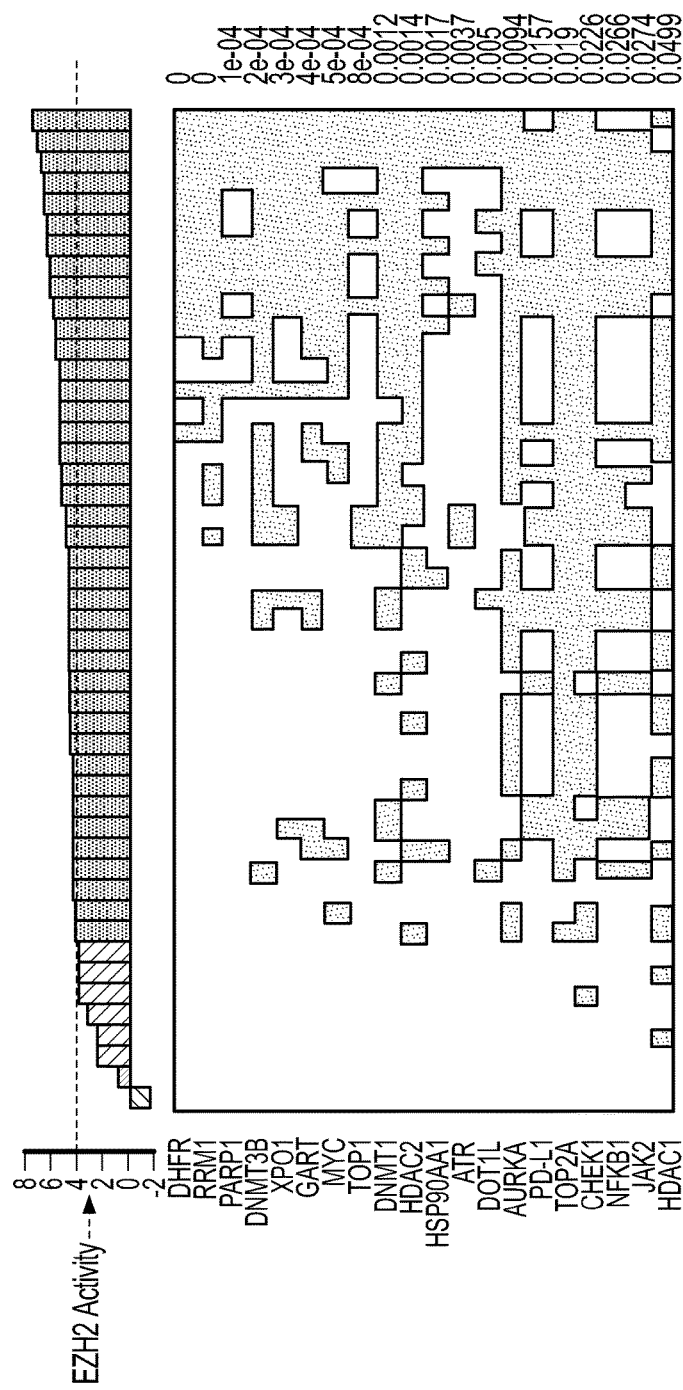
Figure 6F:
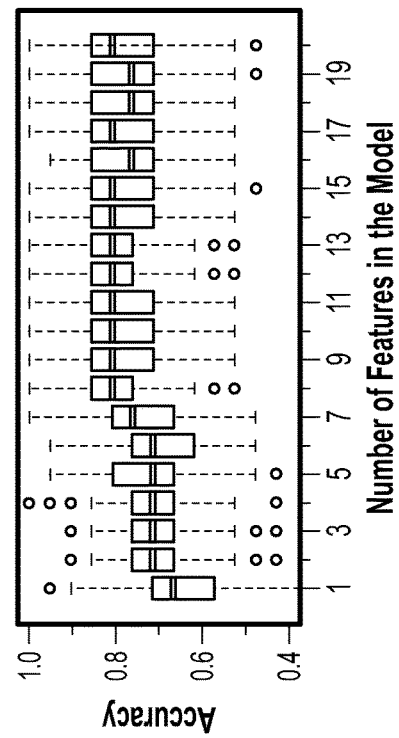

Differential protein activity on 48 TCGA DLBCL primary patient samples was inferred using a pan-TCGA reference to compute gene expression signatures followed by interrogation with metaVIPER. The majority (81%) of DLBCL tumors demonstrate significantly increased EZH2 activity (Bonferroni p-value<0.01), in spite of only a few of the tumors harboring mutations in EZH2, suggesting that EZH2 may represent a unique vulnerability in DLBCL. Unbiased co-segregation analysis between EZH2 and a set of 400 'druggable' proteins demonstrated that the aberrant activity of several proteins are strongly associated with EZH2 activation, including HDAC 1/2 and DNMT (FIG. 6F), further supporting dual targeting of EZH2 and HDACs in DLBCL. Taken together, interrogation of protein activity as a means to identify essential pathways that are common among synergistic cell lines describe a cellular state that is characterized by a 1. high level of proliferation; 2. transcriptional silencing through chromatin remodeling/condensation; 3. halt in cellular differentiation; and lastly; 4. suppression of inflammatory response. TGFβ signaling, which promotes T-regulatory cell function, is found to be more enriched in non-synergistic cell lines.

Figure 6G:
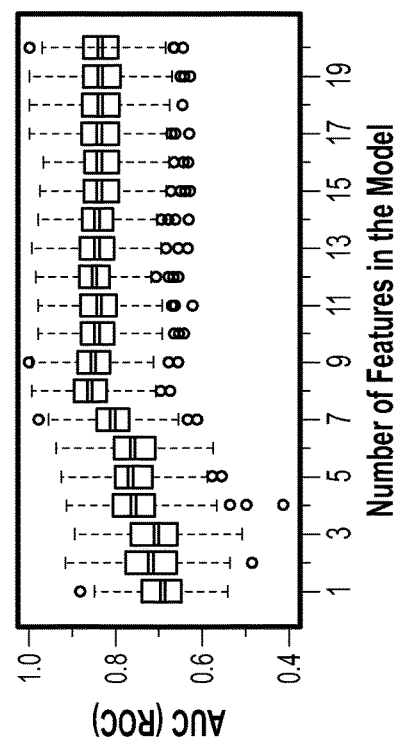

VIPER inference of protein activity is highly reproducible and biologically relevant. We developed a random forest classifier from the basal protein activity profiles of this diverse set of lymphoma cell lines to predict synergy between GSK126 and romidepsin. This classifier demonstrated good receiver operating characteristics on 3-fold cross validation, with an AUC of 0.89 and an accuracy rate of 0.83 for predicting synergy (FIG. 6G). The classifier plateaued in performance with the inclusion of only 8 proteins, consistent with the ability of VIPER to identify biologically relevant proteins. Interestingly, decreased activity of KAT2B, an important HAT protein, was one of the most prominent features in the classifier for predicting synergistic activity of GSK126 and romidepsin.

Discussion

Epigenetic alterations have been implicated as drivers of lymphomagenesis. Given the prominence of EZH2 dysregulation in lymphoma and other malignancies, selective EZH2 inhibitors have been developed and have shown promising single-agent activity in early clinical studies[13,15]. HAT mutations can lead to haploinsufficiency of histone acetylation inducing transcriptional inhibition[17].

We describe that the combination of GSK126 and romidepsin is highly synergistic in EZH2 dysregulated lymphoma cell lines secondary to disassembly of the PRC2 complex due to acetylation of RbAP 46/48. This in turn causes attenuation of H3K27 methylation, increased acetylation, upregulation of p21, which together triggers apoptosis.

Acetylation of tumor suppressors and oncogenes has been described[18,28]. EZH2 has been shown to be directly acetylated by P300/CBP-associated factor (PCAF) and deacetylated by SIRT1 in lung adenocarcinoma models, with acetylation of EZH2 having no effects on EZH2's ability to interact with other members of the PRC2 complex[29]. We demonstrate that exposure to GSK126 and romidepsin leads to acetylation of RbAP 46/48, in turn, causing instability of the PRC2 complex, preventing EZH2 from catalyzing trimethylation, leading to an open chromatin state.

The combination of GSK126 and romidepsin is highly synergistic in EZH2 dysregulated lymphoma cell lines secondary to disassembly of the PRC2 complex due to acetylation of RbAP 46/48. This in turn causes attenuation of H3K27 methylation, increased acetylation, upregulation of p21, which together triggers apoptosis. In vivo experiments demonstrated improvement in overall survival and tumor growth delay favoring the combination arm. EZH2 dysfunction as represented by activating mutations and overexpression are present in NHL. EZH2 is able to catalyze H3K27me3, a mark of transcriptional repression, and is also able to recruit HDACs to further inhibit transcription. Loss of function mutations in HATs are found in NHL, and are specifically frequent in DLBCL. These inactivating mutations promote a deacetylated state leading to chromatin condensation.

With the use of next-generation sequencing, individualized approaches to cancer therapy may arise based on unique gene expression patterns and mutational profiles that collectively contribute to a specific molecular phenotype. In an effort to identify a gene expression profile that may select patients that would benefit from dual EZH2 and HDAC inhibition, pre-treatment RNA sequencing on a panel of lymphoma cell lines was performed. Cell lines demonstrating synergy to combined epigenetic therapy share a common basal genetic signature with enrichment in chromatin remodeling and gene silencing pathways, with identification of 69 genes that are expressed in a similar pattern. Using metaVIPER, enrichment of chromatin modification and epigenetic pathways was verified, but it also identified enrichment of DNA repair/synthesis and cell cycle regulation pathways as well as downregulation of immune/inflammatory pathways in synergistic cell lines as compared to non-synergistic cell lines.

REFERENCES

1. Bracken A P, Helin K. Polycomb group proteins: navigators of lineage pathways led astray in cancer. Nat Rev Cancer 2009; 9:773-84.
2. Vire E, Brenner C, Deplus R, et al. The Polycomb group protein EZH2 directly controls DNA methylation. Nature 2006; 439:871-4.
3. van der Vlag J, Otte A P. Transcriptional repression mediated by the human polycomb-group protein EED involves histone deacetylation. Nature genetics 1999; 23:474-8.
4. Morin R D, Johnson N A, Severson T M, et al. Somatic mutations altering EZH2 (Tyr641) in follicular and diffuse large B-cell lymphomas of germinal-center origin. Nature genetics 2010; 42:181-5.
5. Bodor C, O'Riain C, Wrench D, et al. EZH2 Y641 mutations in follicular lymphoma. Leukemia 2011; 25:726-9.
6. Zhang X, Chen X, Lin J, et al. Myc represses miR-15a/miR-16-1 expression through recruitment of HDAC3 in mantle cell and other non-Hodgkin B-cell lymphomas. Oncogene 2012; 31:3002-8.
7. Ntziachristos P, Tsirigos A, Van Vlierberghe P, et al. Genetic inactivation of the polycomb repressive complex 2 in T cell acute lymphoblastic leukemia. Nature medicine 2012; 18:298-301.
8. Fujikawa D, Nakagawa S, Hori M, et al. Polycomb-dependent epigenetic landscape in adult T-cell leukemia. Blood 2016; 127:1790-802.
9. Yang X P, Jiang K, Hirahara K, et al. EZH2 is crucial for both differentiation of regulatory T cells and T effector cell expansion. Sci Rep 2015; 5:10643.
10. Knutson S K, Kawano S, Minoshima Y, et al. Selective inhibition of EZH2 by EPZ-6438 leads to potent antitumor activity in EZH2-mutant non-Hodgkin lymphoma. Molecular cancer therapeutics 2014; 13:842-54.
11. McCabe M T, Ott H M, Ganji G, et al. EZH2 inhibition as a therapeutic strategy for lymphoma with EZH2-activating mutations. Nature 2012; 492:108-12.
12. McCabe M T, Graves A P, Ganji G, et al. Mutation of A677 in histone methyltransferase EZH2 in human B-cell lymphoma promotes hypertrimethylation of histone H3 on lysine 27 (H3K27). Proceedings of the National Academy of Sciences of the United States of America 2012; 109:2989-94.
13. Italiano A, Soria J-C, Toulmonde M, et al. Tazemetostat, an EZH2 inhibitor, in relapsed or refractory B-cell non-Hodgkin lymphoma and advanced solid tumours: a first-in-human, open-label, phase 1 study. The Lancet Oncology.
14. Morschhauser F, Salles G, McKay P, et al. INTERIM REPORT FROM A PHASE 2 MULTICENTER STUDY OF TAZEMETOSTAT, AN EZH2 INHIBITOR, IN PATIENTS WITH RELAPSED OR REFRACTORY B-CELL NON-HODGKIN LYMPHOMAS. Hematological Oncology 2017; 35:24-5.
15. Harb W, Abramson J, Lunning M, et al. 42OA phase 1 study of CPI-1205, a small molecule inhibitor of EZH2, preliminary safety in patients with B-cell lymphomas. Annals of Oncology 2018; 29:mdy048.01-mdy.01.
16. Pasqualucci L, Dominguez-Sola D, Chiarenza A, et al. Inactivating mutations of acetyltransferase genes in B-cell lymphoma. Nature 2011; 471:189-95.
17. Andersen C L, Asmar F, Klausen T, Hasselbalch H, Gronbaek K. Somatic mutations of the CREBBP and EP300 genes affect response to histone deacetylase inhibition in malignant DLBCL clones. Leukemia research reports 2012; 2:1-3.
18. Amengual J E, Clark-Garvey S, Kalac M, et al. Sirtuin and pan-class I/II deacetylase (DAC) inhibition is synergistic in preclinical models and clinical studies of lymphoma. Blood 2013; 122:2104-13.
19. Kalac M, Scotto L, Marchi E, et al. HDAC inhibitors and decitabine are highly synergistic and associated with unique gene-expression and epigenetic profiles in models of DLBCL. Blood 2011; 118:5506-16.
20. Marchi E, Paoluzzi L, Scotto L, et al. Pralatrexate is synergistic with the proteasome inhibitor bortezomib in in vitro and in vivo models of T-cell lymphoid malignancies. Clinical cancer research: an official journal of the American Association for Cancer Research 2010; 16:3648-58.
21. Borisy A A, Elliott P J, Hurst N W, et al. Systematic discovery of multicomponent therapeutics. Proceedings of the National Academy of Sciences of the United States of America 2003; 100:7977-82.
22. Berenbaum M C. Criteria for analyzing interactions between biologically active agents. Advances in cancer research 1981; 35:269-335.
23. Paoluzzi L, Gonen M, Gardner J R, et al. Targeting Bcl-2 family members with the BH3 mimetic AT-101 markedly enhances the therapeutic effects of chemotherapeutic agents in vitro and in vivo models of B-cell lymphoma. Blood 2008; 111:5350-8.
24. Nekrasov M, Wild B, Muller J. Nucleosome binding and histone methyltransferase activity of *Drosophila* PRC2. EMBO reports 2005; 6:348-53.

25. Zullo K, Scotto L, Amengual J E, O'Connor O A. The Aurora A Kinase Inhibitor, Alisertib, Has Broad Activity In Nonclinical Models Of T-Cell Lymphoma and Is Highly Synergistic With Romidepsin, But Not With Pralatrexate Or The Proteasome Inhibitor, Ixazomib 2013.
26. Gao J, Aksoy B A, Dogrusoz U, et al. Integrative analysis of complex cancer genomics and clinical profiles using the cBioPortal. Science signaling 2013; 6:p11.
27. Shen Y, Alvarez M J, Bisikirska B, et al. Systematic, network-based characterization of therapeutic target inhibitors. PLoS computational biology 2017; 13:e1005599.
28. Bereshchenko O R, Gu W, Dalla-Favera R. Acetylation inactivates the transcriptional repressor BCL6. Nature genetics 2002; 32:606-13.
29. Wan J, Zhan J, Li S, et al. PCAF-primed EZH2 acetylation regulates its stability and promotes lung adenocarcinoma progression. Nucleic acids research 2015; 43:3591-604.
30. Brault L, Menter T, Obermann E C, et al. PIM kinases are progression markers and emerging therapeutic targets in diffuse large B-cell lymphoma. British journal of cancer 2012; 107:491-500.
31. Drexler H G, Eberth S, Nagel S, MacLeod R A. Malignant hematopoietic cell lines: in vitro models for double-hit B-cell lymphomas. Leukemia & lymphoma 2016; 57:1015-20.
32. Peng D, Kryczek I, Nagarsheth N, et al. Epigenetic silencing of TH1-type chemokines shapes tumour immunity and immunotherapy. Nature 2015; 527:249-53.
33. Casey S C, Tong L, Li Y, et al. MYC regulates the antitumor immune response through CD47 and PD-L1. Science 2016; 352:227-31.
34. Schmitz R, Wright G W, Huang D W, et al. Genetics and Pathogenesis of Diffuse Large B-Cell Lymphoma. N Engl J Med 2018; 378:1396-407.
35. Chapuy B, Stewart C, Dunford A J, et al. Molecular subtypes of diffuse large B cell lymphoma are associated with distinct pathogenic mechanisms and outcomes. Nature medicine 2018; 24:679-90.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of treating lymphoma in a subject in need thereof, the method comprising administering an Enhancer of Zeste Homolog 2 (EZH2) inhibitor and a histone deacetyltransferase (HDAC) inhibitor to the subject, wherein the EZH2 inhibitor is tazemetostat and the HDAC inhibitor is belinostat.

2. The method of claim 1, wherein the lymphoma is an EZH2-dysregulated lymphoma.

3. The method of claim 1, wherein the EZH2 inhibitor and the HDAC inhibitor are administered simultaneously, sequentially or separately.

4. The method of claim 1, wherein the administration of the EZH2 inhibitor and the HDAC inhibitor produces a synergistic effect on the lymphoma compared to an effect of the EZH2 inhibitor alone or an effect of the HDAC inhibitor alone.

5. The method of claim 4, wherein the administration of the EZH2 inhibitor and the HDAC inhibitor results in a synergistic increase in apoptosis of cancer cells and/or a synergistic reduction in tumor volume.

6. The method of claim 1, wherein the EZH2 inhibitor and/or the HDAC inhibitor are administered orally, intravenously, intramuscularly, topically, arterially, or subcutaneously.

7. The method of claim 1, wherein the subject is a human.

8. The method of claim 1, wherein the subject tests positive for an EZH2 gene mutation.

9. The method of claim 8, wherein the EZH2 gene mutation results in EZH2 overexpression.

10. The method of claim 2, wherein the EZH2-dysregulated lymphoma comprises a gain-of-function mutation in an EZH2 gene.

11. The method of claim 2, wherein the EZH2-dysregulated lymphoma is germinal center (GC) derived lymphoma.

12. The method of claim 2, wherein the EZH2-dysregulated lymphoma is germinal center (GC) diffuse large B-cell lymphoma (GC-DLCBL), or adult T-cell leukemia lymphoma (ATLL).

13. The method of claim 1, wherein the lymphoma is diffuse large B-cell lymphoma (DLCBL) or activated B-Cell (ABC) diffuse large B-cell lymphoma (ABC-DLCBL).

14. The method of claim 1, wherein the lymphoma is relapsed or refractory lymphoma, B-cell lymphoma, T-cell lymphoma, GC-derived B-cell lymphoma, follicular lymphoma (FL), mantle cell lymphoma (MCL), mutant follicular lymphoma, and/or double-hit lymphoma.

15. A method of treating lymphoma cells in vitro, comprising contacting the lymphoma cells with an EZH2 inhibitor and an HDAC inhibitor, wherein the EZH2 inhibitor is tazemetostat and the HDAC inhibitor is belinostat.

* * * * *